(12) United States Patent
Kayser et al.

(10) Patent No.: US 11,758,931 B2
(45) Date of Patent: *Sep. 19, 2023

(54) CHARACTERISTICS OF MEAT PRODUCTS

(71) Applicant: Upside Foods, Inc., Berkeley, CA (US)

(72) Inventors: Kevin J. Kayser, Chesterfield, MO (US); Morgan Laurence Rease, Emeryville, CA (US); Mark E. Juhas, Berkeley, CA (US); Jessica M. Joslin, Emeryville, CA (US); Uma S. Valeti, St. Paul, MN (US); Eric N. Schulze, San Francisco, CA (US)

(73) Assignee: UPSIDE FOODS, INC., Berkeley, CA (US)

( * ) Notice: Subject to any disclaimer, the term of this patent is extended or adjusted under 35 U.S.C. 154(b) by 166 days.

This patent is subject to a terminal disclaimer.

(21) Appl. No.: 17/482,282

(22) Filed: Sep. 22, 2021

(65) Prior Publication Data

US 2022/0071247 A1 Mar. 10, 2022

Related U.S. Application Data

(63) Continuation of application No. 17/033,635, filed on Sep. 25, 2020.

(60) Provisional application No. 62/970,109, filed on Feb. 4, 2020.

(51) Int. Cl.

| | |
|---|---|
| *A23L 13/00* | (2016.01) |
| *A23L 33/12* | (2016.01) |
| *A23L 33/175* | (2016.01) |
| *A23L 33/15* | (2016.01) |
| *A23L 13/50* | (2016.01) |
| *C12Q 1/06* | (2006.01) |
| *C12N 5/071* | (2010.01) |
| *C12N 5/00* | (2006.01) |
| *C12N 5/077* | (2010.01) |

(52) U.S. Cl.
CPC ............. *A23L 13/00* (2016.08); *A23L 13/50* (2016.08); *A23L 33/12* (2016.08); *A23L 33/15* (2016.08); *A23L 33/175* (2016.08); *C12N 5/0031* (2013.01); *C12N 5/0602* (2013.01); *C12N 5/0656* (2013.01); *C12N 5/0658* (2013.01); *C12Q 1/06* (2013.01); *C12N 5/0037* (2013.01)

(58) Field of Classification Search
CPC ........ A23L 13/00; A23L 33/00; A23L 33/115; A23L 33/12; A23L 33/175; C12Q 1/06; C12Q 1/10

See application file for complete search history.

(56) References Cited

U.S. PATENT DOCUMENTS

| | | |
|---|---|---|
| 6,579,549 B1 | 6/2003 | Thrasher et al. |
| 7,001,633 B2 | 2/2006 | Pasch et al. |
| 7,270,829 B2 | 9/2007 | Eelen |
| 7,476,409 B2 | 1/2009 | Sinah et al. |
| 7,476,410 B2 | 1/2009 | Singh et al. |
| 7,661,355 B2 | 2/2010 | Kremer |
| 9,408,407 B2 | 8/2016 | Shekdar et al. |
| 10,674,740 B2 | 6/2020 | Tornelund et al. |
| 2002/0054942 A1 | 5/2002 | Olson et al. |
| 2005/0058751 A1 | 3/2005 | Brotsky et al. |
| 2006/0029922 A1 | 2/2006 | Van Eelen et al. |
| 2009/0068316 A1 | 3/2009 | Phelps et al. |
| 2010/0173061 A1 | 7/2010 | Wilkes |
| 2014/0093618 A1* | 4/2014 | Forgacs ............... C12N 5/0062 426/92 |
| 2014/0113029 A1 | 4/2014 | Timm et al. |
| 2016/0227830 A1 | 8/2016 | Genovese et al. |
| 2016/0251625 A1 | 9/2016 | Genovese et al. |
| 2017/0035076 A1 | 2/2017 | Geistlinger et al. |
| 2019/0024079 A1 | 1/2019 | Genovese et al. |
| 2019/0075820 A1 | 3/2019 | Redl et al. |
| 2019/0174778 A1 | 6/2019 | Van Dorn |
| 2020/0140810 A1 | 5/2020 | Ben-Arye et al. |
| 2020/0165569 A1 | 5/2020 | Genovese et al. |
| 2021/0106032 A1 | 4/2021 | Leung et al. |
| 2021/0145031 A1 | 5/2021 | Leung et al. |
| 2021/0171912 A1 | 6/2021 | Genovese et al. |

(Continued)

FOREIGN PATENT DOCUMENTS

| | | |
|---|---|---|
| CN | 103747693 B | 8/2017 |
| WO | WO 2006/041429 A2 | 4/2006 |
| WO | WO 2009/116864 A1 | 9/2009 |

(Continued)

OTHER PUBLICATIONS

"Uma Valeti from Memphis Meats at EAT Stockholm Food Forum 2017", 2017, YouTube, https://www.youtube.com/watch?v=S2m_YtqkGGk (Year: 2017).*

(Continued)

*Primary Examiner* — Jeffrey P Mornhinweg
*Assistant Examiner* — Kelly P Kershaw
(74) *Attorney, Agent, or Firm* — Fenwick & West LLP

(57) ABSTRACT

The present disclosure provides methods and compositions useful for the production of slaughter-free meat products, and the characterizations of the same. The slaughter-free meat products contain several points of distinction when compared to conventional meat procured by harvesting the tissue of a dead animal. Such points of distinction include, but are not limited to, significantly reduced or substantially no: steroid hormones, antibiotics, or microbial contamination; lower fat content; no vasculature; and extended shelf life both at room temperature and when refrigerated.

17 Claims, 13 Drawing Sheets

(56) References Cited

U.S. PATENT DOCUMENTS

| | | | |
|---|---|---|---|
| 2021/0235733 | A1 | 8/2021 | Kayser et al. |
| 2022/0007695 | A1 | 1/2022 | Kayser et al. |

FOREIGN PATENT DOCUMENTS

| | | |
|---|---|---|
| WO | WO 2013/016547 A2 | 1/2013 |
| WO | WO 2018/011805 A2 | 1/2018 |
| WO | WO 2019/014652 | 1/2019 |
| WO | WO 2019/016795 A1 | 1/2019 |
| WO | WO 2020/243324 | 12/2020 |

OTHER PUBLICATIONS

Watson, E., "Memphis Meats: 'What's common in Silicon Valley is that you move fast and break things, but that's an awful way to approach making food'", 2018, Food Navigator USA.com, <https://www.foodnavigator-usa.com/Article/2018/05/02/Memphis-Meats-VP-Science-does-not-occur-in-a-cultural-vacuum> (Year: 2018).*

Ahmad, R.S., Imran, A., Hussain, M.B., "Nutritional Composition of Meat", 2018, Meat Science and Nutrition, pp. 61-77 (Year: 2018).*

Williams, P.G., "Nutritional composition of red meat", 2007, University of Wollongong (Year: 2007).*

"Substantial", 2019, Meririam-Webster.com, https://web.archive.org/web/20190415070123/https://www.merriam-webster.com/dictionary/substantial (Year: 2019).*

Boz et al., "The carcass traits, carcass nutrient composition, amino acid, fatty acid, and cholesterol contents of local Turkish goose varieties reared in an extensive production system", 2019, Poultry Science, vol. 98, pp. 3067-3080 (Year: 2019).*

Norwicka et al., "Variability in nutritional value of traditional goose meat product", 2018, Animal Science Papers and Reports, vol. 36, No. 4, pp. 405-420 (Year: 2018).*

"Food Data Central", 2019, US DA, https ://fdc.nal.usda.gov/fdc-app.html#/food-details/171077/nutrients.

"Uma Valeti from Memphis Meats at EAT Stockholm Food Forum 2017", 2017, YouTube, https://www.youtube.com/watch?v=S2m_YtqkGGk.

Amaral et al., "Lipid oxidation in meat: mechanisms and protective factors—a review", 2018, Food Science and Technology, vol. 38 (Suppl. 1), pp. 1-15 (Year: 2018).

Barroeta, A.C., "Nutritive value of poultry meat: relationship between vitamin E and PUFA", 2007, World's Poultry Science Journal, pp. 277-284.

Ben-Arye T., "Tissue Engineering for Clean Meat Production," Front. Sustain. Food Syst., Jun. 18, 2019, vol. 3, article 46.

Bhat et al., Prospectus of cultured meat—advancing meat, Journal of Food Science and Technology, vol. 48, No. 2, Dec. 30, 2010, pp. 125-140.

Chriki et al., "The Myth of Cultured Meat: A Review," Frontiers in Nutrition, Feb. 2020, vol. 7, article 7.

Datar and Betti, "Possibilities for an In Vitro Meat Production System," Innovative Food Science & Emerging Technologies 11 (1):13-22(2010).

Dave et al., "Meat Spoilage Mechanisms and Preservation Techniques: A Critical Review," American Journal of Agricultural and Biological Sciences, 2011, 6(4), pp. 486-510.

Doyle E., "Human Safety of Hormone Implants Used to Promote Growth in Cattle," Food Research Institute, Jul. 2000, 24 pages.

Enser, M., "Muscle lipids and meat quality," Division of Food Animal Science, School of Veterinary Science, 2001, pp. 243-246.

Fao, "The production of fish meal and oil," Fisheries Industries Division, Food and Agriculture Organization of the United Nations, Rome, Italy, Fisheries Technical Papers-T142, 1986, 71 pages.

FDA—CFR—Code of Federal Reaulations Title 21, Apr. 1, 2019, 24 paaes.

Feng et al., "BAM Chapter 4: Enumeration of *Escherichia coli* and the *Coliform* Bacteria," retrieved online Feb. 3, 2021, 18 pages, https://www.fda.gov/food/laboratory-methods-food/bam-chapter-4-enumeration-escherichia-coli-and-coliform-bacteria#conventional.

Finnie, "Is Lab Grown Meat the Coup De Gras to the Vegan Argument," Mar. 17, 2016, 3 pages, http://trn.tv/blog/blog/2016/03/17/is-lab-grown-meat-the-coup-de-gras-to-the- veaan-araument/.

Flatow, "Biting Into the First In Vitro Burger," NPR, Aug. 9, 2013, 19 pages.

Gasteratos K., "90 Reasons to Consider Cellular Agriculture," 2019, 27 pages, http://nrs.harvard.edu/urn-3:HUL.InstRepos:38573490.

Gerhardt C. et al., "How Will Cultured Meat and Meat Alternatives Disrupt the Agricultural and Food Industry?" 2019, A.T. Kearney, Inc . . . .

Ghaly et al., "Fish spoilage mechanisms and preservation techniques: Review," Am. J. Applied Sci., 7: 846-864, 2010, ISSN 1546-9239.

Hartwig et al., "Physiological quantities of naturally occurring steroid hormones (androgens and progestogens), precursors and metabolites in beef of differing sexual origin," Z Lebensm Unters Forsch 205, 5-10 (1997).

Ho, S., "10 Reasons Why Cultivated Meat Is The Future Of Protein: The Case For Lab-Grown," May 13, 2020.

Huis, J.H.J., "Microbial and biochemical spoilage of foods: An overview," Int. J. Food Microbiology, 1996, 33: 1-18.

International Search Report and Written Opinion dated May 20, 2021, in International Application No. PCT/US2021/016681, 18 pages.

Kadim et al., "Cultured meat from muscle stem cells: A review of challenges and prospects," Journal of integrative Agriculture, vol. 14, No. 2, Feb. 1, 2015, pp. 222-233.

Kim et al., "Assessment of the Microbial Level for Livestock Products in Retail Meat Shops implementing HACCP System," Korean J Food Sci Anim Resour. Oct. 31, 2016; 36(5): 594-600.

Kim et al., "Monitoring of Microbial Contaminants of Beef, Pork, and Chicken in HACCP Implemented Meat Processing Plants of Korea," Korean J Food Sci Anim Resour. Apr. 2018; 38(2): 282-290.

Kirschner's Korner, "Memphis Meats CEO Discuss the Future of Meat," Nov. 26, 2016, 4 pages, https://kirschnerskorner.com/2016/11/26/uma-valeti-interview/.

Kolkmann et al., "Serum-free media for the growth of primary bovine myoblasts," Cytotechnology, Kluwer Academic Publishers, Dordrecht, NL, vol. 72, No. 1, Dec. 28, 2019, pp. 111-120.

Langelaan, et al., "Meet The New Meat: Tissue Engineered Skeletal Muscle," Trends in Food Science & Technology 21 (2):59-66 (2010).

Mah, "Lab-Grown Meats Will Change the Food Industry Forever," Synthego, May 15, 2019, 20 pages.

Maturin et al., "BAM Chapter 3: Aerobic Plate Count," retrieved online Feb. 3, 2021, 11 pages, https://www.fda.gov/food/laboratory-methods-food/bam-chapter-3-aerobic-plate- count#conventional.

Messing, L., "Handling, Using, & Storing Poultry", 2014, Michigan State University, Extension Bulletin E3232 (Year: 2014).

Microbiological Guidelines: Support for Interpretation of Microbiological . . . By Collective, Section 3.3.1.1. Listeria monocytogenes, 2 pages.

Milicevic et al., "The role of total fats, saturated/unsaturated fatty acids and cholesterol content in chicken meat as cardiovascular risk factors", 2014, Lipids in Health and Disease, 13:42.

Min et al., "Mechanism of Lipid Peroxidation in Meat and Meat Products—A Review," Food Sci. Biotechnol., vol. 14, No. 1, pp. 152-163, Jan. 2005.

Pandurangan, et al. A novel approach for in vitro meat production. Appl Microbial Biotechnol. Jul. 2015; 99(13):5391-5395. doi: 10.1007/s00253-015-6671-5. Epub May 14, 2015.

Post, M., "Cultured Meat From Stem Cells: Challenges and Prospects," Meat Sci. 92(3):297-301 (2012).

Safety assurance during food processing, edited by Frans J.M. Smulders, John D. Collins, published 2004, 3 pages.

Shahidi, F., "Assessment of lipid oxidation and off-flavour development in meat and meat products," In: Flavor of meat and meat products. Chapman and Hall, London, U.K, 1994, pp. 247-266. ISBN: 0-7514-0484-5.

(56) References Cited

OTHER PUBLICATIONS

Simitzis, P.E. and S.G. Deligeorgis, "Lipid oxidation of meat and use of essential oils as antioxidants in meat products," 2010.

Specht L., "Is the Future of Meat Animal-Free?" Food Technology Magazine, Jan. 1, 2018, 18 pages.

Stephens et al., Bringing cultured meat to market: Technical, socio-political, and regulatory challenges in cellular agriculture, Trends in Food Science & Technology, vol. 78, Aug. 2018, pp. 155-166.

Strakova et al., "Differences in the amino acid composition of muscles from pheasant and broiler chickens", 2006, Arch. Tierz., Dummerstorf, vol. 49, 5, pp. 508-514.

Swientek, "Meat production without animals," Jun. 27, 2017, 4 pages.

Synthetic Meat on Our Tables by 2021. Are We Ready?, Apr. 3, 2020, Flick on Food, 4 pages, https://www.flickonfood.com/en/synthetic-meat-on-our-tables-by-2021-are-we-ready/.

Toldra, "The role of muscle enzymes in dry-cured meat products with different drying conditions," Trends in Food Science & technology, Apr. 2006;17(4):164-168.

Valeti, U., "The Opposite of a Slaughter House," 5 pages, https://eatforum.org/learn-and-discover/the-opposite-of-a-slaughter-house-dr-uma-valeti/.

Watson, "Cell-based meat cos: Please stop calling us 'lab-grown' meat. and we don't use antibiotics in full-scale production," Oct. 25, 2018, 5 pages https://www.foodnavigator-usa.com/article/2018/10/25/cell-based-meat-cosplease-stop-calling-us-lab-grown-meat-and-we-don-t-use-antibiotics-infull-scale-production.

Watson, E., "Memphis Meats: 'What's common in Silicon Valley is that you move fast and break things, but that's an awful way to approach making food'", 2018, Food Navigator USA.com, <https://www.foodnavigator-usa.com/Article/2018/05/02/Memphis-Meats-VP-Science-does-not-occur-in-a-cultural-vacuum>.

Zaraska, M., "Is Lab-Grown Meat Good for Us?" The Atlantic, Aug. 19, 2013, 5 pages.

Brunner, D. et al. "Serum-Free Cell Culture: The Serum-Free Media Interactive Online Database." ALTEX: Alternative to Animal Experimentation, vol. 27, No. 1, Feb. 1, 2010, pp. 53-62.

Costa, A.R. et al., "Strategies for adaptation of mAb-producing CHO cells to serum-free medium," BMC Proceedings, vol. 5(Suppl. 8), Nov. 22, 2011, pp. 1-2.

Nowicka, K. et al. "Variability in Nutritional Value of Traditional Goose Meat Product." Animal Science Papers and Reports, vol. 36, No. 4, 2018, pp. 405-420.

Okruszek, A. et al. "Chemical Composition and Amino Acid Profiles of Goose Muscles from Native Polish Breeds." Poultry Science, vol. 92, No. 4, Apr. 1, 2013, pp. 1127-1133.

United States Office Action, U.S. Appl. No. 17/033,635, dated Oct. 4, 2021, 23 pages.

United States Office Action, U.S. Appl. No. 17/033,635, dated Apr. 21, 2021, 20 pages.

United States Office Action, U.S. Appl. No. 17/033,635, dated Feb. 3, 2021, 22 pages.

United States Office Action, U.S. Appl. No. 17/033,635, dated Jan. 27, 2022, 24 pages.

United States Office Action, U.S. Appl. No. 17/482,286, dated Nov. 9, 2021, 17 pages.

United States Office Action, U.S. Appl. No. 17/482,286, dated Mar. 1, 2022, 20 pages.

Yang, Z. et al. "Culture Conditions and Types of Growth Media for Mammalian Cells." IntechOpen, Biomedical Tissue Culture, 2012, pp. 3-18.

Betti, M. et al., "Processing, Products, and Food Safety: Omega-3-enriched broiler meat: 3. Fatty acid distribution between triacylglycerol and phospholipid classes", Poultry Science, vol. 88, Aug. 2009, pp. 1740-1754.

Bhat, Z.F. et al., "Tissue engineered meat-Future meat," Journal of Stored Products and Postharvest Research 2(1), Jan. 2011, pp. 1-10.

Demeure, O. et al., "Liver X receptor alpha regulates fatty acid synthase expression in chicken", Poultry Science, vol. 88, Dec. 2009, pp. 2628-2635.

Garry, D.J. et al., "Life without myoglobin", Cellular and Molecular Life Sciences, vol. 57, Jun. 2000, pp. 896-898.

happyforks.com, "Canada Goose, breast meat, skinless, raw", Jul. 18, 2017, three pages, [Online] [Retrieved on Jul. 17, 2023] Retrieved from the Internet Archive: <URL: https://web.archive.org/web/20170718212445/https://happyforks.com/food/canada-goose/8764>.

Reynolds, M. "The Clean Meat Industry is Racing to Ditch its Reliance on Foetal Blood." Wired UK, Science, Mar. 20, 2010, 9 pages, [Online] [Retrieved Jul. 13, 2022], Retrieved from the Internet <URL:https://www.wired.co.uk/article/scaling-clean-meat-serum-just-finless-foods-mosa-meat>.

United States Office Action, U.S. Appl. No. 17/482,286, dated Sep. 14, 2022, 25 pages.

United States Office Action, U.S. Appl. No. 17/482,286, dated Mar. 28, 2023, 33 pages.

United States Office Action, U.S. Appl. No. 17/033,635, dated Nov. 22, 2022, 27 pages.

United States Office Action, U.S. Appl. No. 17/033,635, dated Mar. 13, 2023, 36 pages.

* cited by examiner

CHARACTERISTICS OF MEAT PRODUCTS

CROSS REFERENCE TO RELATED APPLICATIONS

This application is a continuation of U.S. patent application Ser. No. 17/033,635, filed Sep. 25, 2020, which claims priority to U.S. Provisional Patent Application No. 62/970,109, filed on Feb. 4, 2020, the contents of which are incorporated herein by reference in their entireties.

BACKGROUND

Animal meat is a first-choice source of protein for many people all over the world. The total estimated consumption of meat (chicken, turkey, veal, lamb, beef, pork) in 2018 in the USA was 219 lb per capita. It is expected that the traditional (conventional) method of harvesting meat from slaughtered animals, such as livestock, poultry, and fish, usually involving slaughter, may not be sufficient to meet the future demand for meat. Additionally, meat production from these sources is associated with several drawbacks, although legally acceptable, such as increased levels of microbial contamination, and exposure to the hormones and antibiotics traditionally found in conventional meat products. Conventional meat production is also associated with environmental drawbacks such as poor conversion of caloric inputs, greenhouse gas emissions, land usage, water usage, and local pollution. One alternative to conventional meat production involving slaughter is the production of meat by culturing metazoan cells in the laboratory (also referred to herein interchangeably as cell-based meat, cell-based meat, cell culture-based meat, cell-based meat, cell-based meat, or cultured meat).

Adoption of cell-based meat products into the food supply chain will depend on a variety of factors such as the quantifiable features of the meat itself, including, but not limited to, the macro and micro nutrient profiles, levels of hormones, and antibiotics, and shelf life. Comparisons to conventional products will need to be made to ensure comparable nutrient profiles, while seeking out distinguishable factors, such as low/no hormonal or antibiotic content and microbial counts. Cell-based meat products are not yet commercially available but ultimately regulatory bodies will also require quantification and accountability of the meat products intended for the market, food safety establishment prior to sale as well as post-market compliance of the meat products intended for the market.

Production of cell-based meat and customizations to flavor and texture still remain limited by several factors, consistent and methodical production being a few. Provided herein are compositions and methods that address this and other related needs.

SUMMARY

Provided herein are methods and compositions related to the production of slaughter-free meat products generated from cells grown in culture; these meat products are interchangeably referred to herein as cell-based meat products.

In one aspect, provided herein is a slaughter-free meat product for dietary consumption exhibiting an extended shelf life, wherein the shelf life is extended for varying durations following harvest, when compared to conventional meat obtained by slaughter. In a related aspect, provided herein is a slaughter-free meat product for dietary consumption exhibiting a lower microbial contamination count as compared to conventional meat obtained by slaughter, wherein the lower microbial contamination count is exhibited for varying durations following harvest. The slaughter-free meat product may be of any species as disclosed herein.

Also provided herein are methods of generating the slaughter-free meat products of the disclosure, comprising culturing cells such as fibroblasts, myoblasts, adipocytes, endothelial cells, cells of a mesodermal lineage, and combinations thereof, in either suspension culture, or in adherent formats.

DETAILED DESCRIPTION

Figure 1:
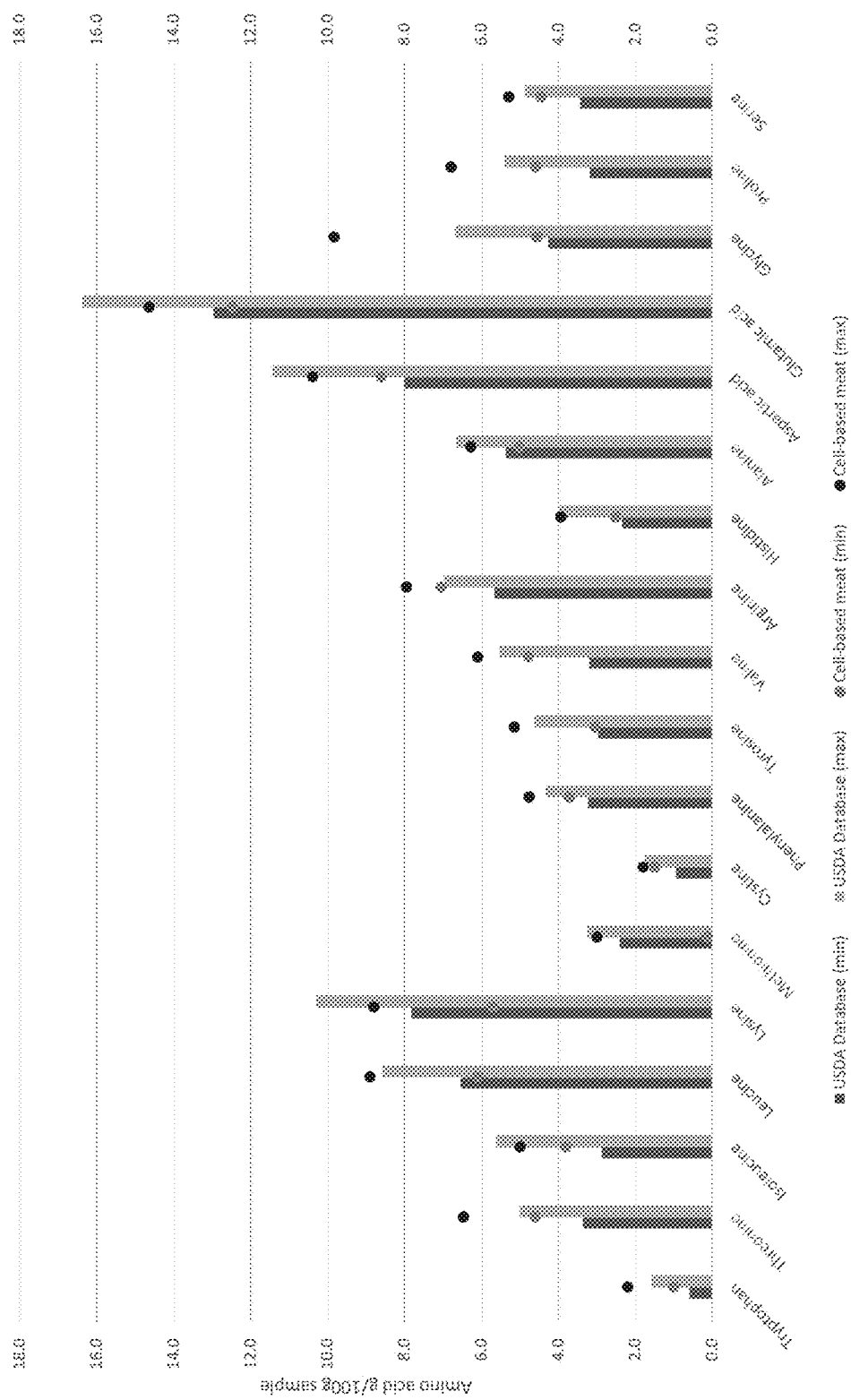
FIG. 1 shows the amino acid profiles found in exemplary slaughter-free, cell-based meat samples, as compared to conventional meat. The USDA database includes amino acid data from: bluefin tuna, tilapia, yellowfin tuna, turkey, lamb, chicken, beef, cornish game hens, guinea fowl, pheasant, quail, squab, goose, duck, ostrich, beef top sirloin, beef short ribs, beef shank, chicken breast, chicken thigh, pork shoulder, grass fed bison, chicken wing, chicken neck, turkey breast, turkey wing, turkey thigh, and lamb shank.

Provided herein are methods and compositions related to the slaughter-free production of meat products, and rely on the use of cell culture based methods for the growth, harvesting, and formulation of cells into meat products. There are several differences in the slaughter-free meat products of the disclosure when compared to conventional meat obtained by slaughter, and these differences are described throughout.

Before describing particular embodiments in detail, it is to be understood that the disclosure is not limited to the particular embodiments described herein, which can vary. It is also to be understood that the terminology used herein is for the purpose of describing particular illustrative embodiments only, and is not intended to be limiting unless otherwise defined. The terms used in this specification generally have their ordinary meaning in the art, within the context of this disclosure and in the specific context where each term is used. Certain terms are discussed below or elsewhere in the specification to provide additional guidance to the practitioner in describing the compositions and methods of the invention and how to make and use them. The scope and meaning of any use of a term will be apparent from the specific context in which the term is used. As such, the definitions set forth herein are intended to provide illustrative guidance in ascertaining particular embodiments of the invention, without limitation to particular compositions or biological systems.

As used in the present disclosure and the appended claims, the singular forms "a," "an" and "the" include plural references unless the content clearly dictates otherwise.

Throughout the present disclosure and the appended claims, unless the context requires otherwise, the word "comprise", or variations such as "comprises" or "comprising", will be understood to imply the inclusion of a stated element or group of elements but not the exclusion of any other element or group of elements.

The term "edible" in the context of the cell-based meat as used herein encompasses raw or uncooked meat as well as partially or fully cooked meat.

Unless specific definitions are provided, the nomenclature utilized in connection with, and the laboratory procedures and techniques of, molecular biology, cell biology, analytical chemistry, and synthetic organic chemistry described herein are those well-known and commonly used in the art. Standard techniques may be used for recombinant technology, molecular biological, microbiological, chemical syntheses, and chemical analyses.

The term "slaughter" as applied to the manner in which conventional meat is obtained covers all methods traditionally used to kill an animal, with the purpose of directly harvesting its meat for dietary consumption.

The term "slaughter-free" as applied to the cell based meat products of the disclosure refer to the process by which the meat is generated, starting with cells in culture, and that method which does not involve the slaughter of an animal in order to directly obtain meat from that animal for dietary consumption. It is understood that in some embodiments, it is possible that the starting cells for use in the cell culture methods may have been obtained following the slaughter of an animal, or a biopsy—although the starting cells for use in culture may have been obtained in this manner, the meat resulting from the culturing of cells, by harvest and a possible subsequent formulation are still considered to be meat obtained in a slaughter-free manner. It is noted that as a general matter, as used herein, harvesting of the slaughter-free cell-based meat product may involve using a buffered solution of water (or other aqueous solution) to remove the meat where it is grown (e.g. the surface of a bioreactor, or in a container comprising a the cells cultured in suspension), and the meat may then captured in a collection device (e.g. net, sieve, colander). In some embodiments the meat may be harvested by physical methods (such as scraping), enzymatic methods, and/or chemical methods. In some embodiments the meat may be harvested by any of the above mentioned methods and subsequently rinsed with buffered solutions (or other aqueous solutions).

The phrases "cell-based meat", "slaughter-free cell-based meat", "in vitro produced meat", "in vitro cell-based meat", "cultured meat", "slaughter-free cultured meat", "in vitro produced cultured meat", "in vitro meat", "in vitro cultured meat" and other similar such phrases are interchangeably used herein, and refer to the meat that is generated in vitro, starting with cells in culture, and that method which does not involve the slaughter of an animal in order to directly obtain meat from that animal for dietary consumption.

I. GENERATION OF SLAUGHTER-FREE CELL-BASED MEAT

Provided herein are methods to produce cell-based meat products in a slaughter-free manner.

A. Cells

The slaughter-free cell-based meat products of the disclosure are compositions produced by the culturing of naturally occurring, transgenic, or modified cells in culture.

The cells used in the methods of the present disclosure can be primary cells, or cell lines. The methods provided herein are applicable to any metazoan cell in culture. Generally, the cells can be from any metazoan species whose tissues are suitable for dietary consumption. In some embodiments, the cells demonstrate the capacity for skeletal muscle tissue specification (e.g. myoblasts). In other embodiments, the cells do not demonstrate the capacity for skeletal muscle tissue specification.

In some embodiments, the cells are derived from any non-human animal species intended for human or non-human dietary consumption. In some embodiments the cells may be of avian, ovine, caprine, porcine, bovine, or piscine origin. In some embodiments the cells may be of livestock, poultry, avian, game, or aquatic species.

In some embodiments, the cells are from livestock such as domestic cattle, pigs, sheep, goats, camels, water buffalo, rabbits and the like. In some embodiments, the cells are from poultry such as domestic chicken, turkeys, ducks, geese, pigeons and the like. In some embodiments, the cells are from game species such as wild deer, gallinaceous fowl, waterfowl, hare and the like. In some embodiments, the cells are from aquatic species or semi-aquatic species harvested commercially from wild fisheries or aquaculture operations, or for sport, including certain fish, crustaceans, mollusks, cephalopods, cetaceans, crocodilians, turtles, frogs and the like.

In some embodiments, the cells are from exotic, conserved or extinct animal species. In some embodiments, the cells are from *Gallus gallus, Gallus domesticus, Bos taurus, Sous scrofa, Meleagris gallopavo, Anas platyrynchos, Salmo salar, Thunnus thynnus, Ovis aries, Coturnix, Capra*

*aegagrus hircus*, or *Homarus americanus*. Accordingly, exemplary slaughter-free cell-based meat products of the disclosure include avian meat products, chicken meat products, duck meat products, and bovine meat products.

In some embodiments, the cells are primary stem cells, self-renewing stem cells, embryonic stem cells, pluripotent stem cells, induced pluripotent stem cells, or transdifferentiated pluripotent stem cells.

In some embodiments, the cells are modifiable by a genetic switch to induce rapid and efficient conversion of the cells to skeletal muscle for cultured meat production.

In some embodiments, the cells are myogenic cells, destined to become muscle, or muscle-like cells. In some embodiments, the myogenic cells are natively myogenic, e.g. myoblasts. Natively myogenic cells include, but are not limited to, myoblasts, myocytes, satellite cells, side population cells, muscle derived stem cells, mesenchymal stem cells, myogenic pericytes, or mesoangioblasts.

In some embodiments, cells are of the skeletal muscle lineage. Cells of the skeletal muscle lineage include myoblasts, myocytes, and skeletal muscle progenitor cells, also called myogenic progenitors that include satellite cells, side population cells, muscle derived stem cells, mesenchymal stem cells, myogenic pericytes, and mesoangioblasts.

In some embodiments, the cells are non-myogenic, and such non-myogenic cells can be programmed to be myogenic, for example the cells may comprise fibroblasts modified to express one or more myogenic transcription factors. In exemplary embodiments, the myogenic transcription factors include MYOD1, MYOG, MYF5, MYF6, PAX3, PAX7, paralogs, orthologs, and genetic variants thereof. In some embodiments, the cells are modified to express one or more myogenic transcription factors as described in a PCT publication, WO/2015/066377, incorporated by reference herein in its entirety.

In some embodiments, the cells comprise a mixture of cell populations described herein, e.g. a mixture of fibrogenic cells and myogenic cells in co-culture, e.g. a mixture of fibroblasts and myoblasts in co-culture. In some embodiments the cells used for the production of cell-based meat are a mixture of fibroblasts and myoblasts in a suspension co-culture. In some embodiments the cells used for the production of cell-based meat are a mixture of fibroblasts and myoblasts in an adherent co-culture. In some embodiments cells in co-culture comprise additional cell types such as adipocytes, endothelial cells, and generally cells from the mesoderm lineage.

In some co-culture embodiments, the cells are in a suspension co-culture, in some embodiments, the cells are in an adherent co-culture, and in some embodiments, the culturing processing makes use of both techniques. The co-cultures provide herein comprise a mixture of at least fibroblasts and myoblasts. In some embodiments, the ratio of the fibroblasts to myoblasts (designated as F and M) ranges from about 5F:95M to about 95F:5M. In exemplary embodiments, the ratio of the fibroblasts to myoblasts is about 5F:95M, 10F:90M, 15F:85M, 20F:80M, 25F:75M, 30F:70M, 35F:65M, 40F:60M, 45F:55M, 50F:50M, 55F:45M, 60F:40M, 65F:35M, 70F:30M, 75F:25M, 80F:20M, 85F:15M, 90F:10M, or even about 95F:5M.

In some embodiments, the cells are genetically modified to inhibit a pathway, e.g. the HIPPO signaling pathway. Exemplary methods to inhibit the HIPPO signaling pathway as described in a PCT Application No. PCT/US2018/031276, incorporated by reference herein in its entirety.

In some embodiments, the cells are modified to express telomerase reverse transcriptase (TERT) and/or inhibit cyclin-dependent kinase inhibitors (CKI). In some embodiments, the cells are modified to express TERT and/or inhibit cyclin-dependent kinase inhibitors as described in a PCT publication, WO 2017/124100, incorporated by reference herein in its entirety.

In some embodiments, the cells are modified to express glutamine synthetase (GS), insulin-like growth factor (IGF), and/or albumin. Exemplary methods of modifying cells to express GS, IGF, and/or albumin are described in a PCT Application No. PCT/US2018/042187 which is incorporated by reference herein in its entirety.

In some embodiments, the cells may comprise any combinations of the modifications described herein.

B. Cultivation Infrastructure

As referred to herein, a cultivation infrastructure refers to the environment in which the cells are cultured or cultivated to provide a two-dimensional or three-dimensional meat product.

A cultivation infrastructure includes but is not limited to a roller bottle, a tube, a cylinder, a flask, a petri-dish, a multi-well plate, a dish, a vat, an incubator, a bioreactor, and an industrial fermenter.

While the cultivation infrastructure itself may have a three-dimensional structure or shape, the cells cultured in the cultivation infrastructure may form a monolayer of cells. Compositions and methods of the present disclosure can promote a three-dimensional growth of metazoan cells in the cultivation infrastructure to provide a scaffold-less self-assembly of a three-dimensional cellular biomass.

A three-dimensional cultivation infrastructure may be sculpted into different sizes, shapes, and forms, as desired, to provide the shape and form for the muscle cells to grow and resemble different types of muscle tissues such as steak, tenderloin, shank, chicken breast, drumstick, lamb chops, fish fillet, lobster tail, etc. The three-dimensional cultivation infrastructure may be made from natural or synthetic biomaterials that are non-toxic so that they may not be harmful if ingested. Natural biomaterials may include, for example, collagen, fibronectin, laminin, or other extracellular matrices. Synthetic biomaterials may include, for example, hydroxyapatite, alginate, polyglycolic acid, polylactic acid, or their copolymers. The three-dimensional cultivation infrastructure may be formed as a solid or semisolid support.

A cultivation infrastructure can be of any scale, and support any volume of cellular biomass and culturing reagents. In some embodiments, the cultivation infrastructure ranges from about 10 µL to about 100,000 L. In exemplary embodiments, the cultivation infrastructure is about 10 µL, about 100 µL, about 1 mL, about 10 mL, about 100 mL, about 1 L, about 10 L, about 100 L, about 1000 L, about 10,000 L, or even about 100,000 L.

In some embodiments, the cultivation infrastructure comprises a substrate. A cultivation infrastructure may comprise a permeable substrate (e.g. permeable to physiological solutions) or an impermeable substrate (e.g. impermeable to physiological solutions). The substrate can be flat, concave, or convex. The substrate may be textured so as to promote cell growth and cell sheet attachment.

In some embodiments, the culturing of cells in the cultivation infrastructure can induce the production of extracellular matrix (ECM) that may act as an autologous scaffold to direct three-dimensional cellular growth, e.g. to direct attachment, proliferation and hypertrophy of cells on a plane perpendicular to the substrate.

In some embodiments, the cultivation infrastructure does not comprise an exogenously added scaffold to promote self-assembly of a three-dimensional cellular biomass. In some embodiments, the cultivation infrastructure does not comprise exogenous scaffolds such as a hydrogel or soft agar.

C. Culturing Conditions

The culturing conditions for the generation of cell-based meat are generally aseptic, and sterile.

Cells can be grown in an adherent culture format to form a cell sheet or can be grown in a suspension culture format to form a cell pellet. Table 1 provides exemplary culture methods for the various meat products that can be produced.

In some embodiments, the media is substantially free of serum or other components derived from an animal.

Accordingly, in some embodiments, provided herein is a method of producing slaughter-free cell-based meat comprising: (a) providing cells from a non-human organism; (b) culturing the cells in media under conditions under which the cells grow in either suspension culture or adherent culture, wherein the media is substantially free of serum and other components derived from an animal; and optionally (c) isolating the cells and producing the slaughter-free meat product. In some embodiments the cells in culture comprise fibroblasts, myoblasts, or a co-culture of fibroblasts and myoblasts; in some embodiments cells in co-culture comprise additional cell types such as adipocytes, endothelial cells, and generally cells from the mesoderm lineage.

In some embodiments, provided herein is a method of producing a slaughter-free meat product exhibiting an extended shelf life and/or lower microbial content compared to conventional meat obtained by slaughter, the method comprising: (a) providing cells from a non-human organism; (b) culturing the cells in media under suspension culture conditions, or adherent culture conditions, wherein the media is substantially free of serum and other components derived from an animal; and optionally (c) isolating the cells and producing the slaughter-free meat product. In some embodiments the cells in culture comprise fibroblasts, myoblasts, or a co-culture of fibroblasts and myoblasts; in some embodiments cells in co-culture comprise additional cell types such as adipocytes, endothelial cells, and generally cells from the mesoderm lineage.

In some embodiments, the cells are grown in a suspension culture, e.g. in a shake flask, and the product of the culture yields a cell pellet. In some embodiments the product may be obtained by physical methods (e.g. centrifugation, gravity-assisted settling), chemical methods, enzymatic methods, sedimentation, concentration, flocculation, and the like. In other embodiments, the cells are grown in adherent culture, and the product of the culture is a cell sheet.

D. Harvesting and Formulation

In some embodiments, the slaughter-free cell-based meat of the disclosure is harvested from a bioreactor (or other cell growth apparatus) and assessed for its properties prior to formulation. In some embodiments, the harvesting is carried out under aseptic conditions (e.g. using sterile gloves and working conditions, in a laminar flow hood).

The slaughter-free cell-based meat of the disclosure may be formulated post-harvest (e.g. manipulated, processed) into a specific edible food type, any variety of products, including, but not limited to, a meatball, patty, surimi, cutlet, sausage, loaf, tender, filet-style products, hot dog, nugget, etc. Slaughter-free cell-based meat formulated products of the disclosure may also include meat that has been seasoned or dried such as jerky or snack-stick type products, e.g. in order to further extend the shelf life. Slaughter-free cell-based meat formulated products of the disclosure may also comprise additional ingredients (additives) such as binders, spices, stabilizers, preservatives, and the like. In exemplary embodiments, formulation includes adding one or more of the following ingredients to the harvested cell-based meat: vital wheat gluten, calcium chloride, iota carrageenan, flavor precursor mix, transglutaminase enzyme powder (maltodextrin, enzyme), protein concentrates, protein isolates, polysaccharides, carrageenans, flavorings, yeast extracts, enzymes, fibers, texturized proteins, pectins, starches.

II. CHARACTERISTICS OF CELL-BASED MEAT

Provided herein are slaughter-free cell-based meat products comprising a number of unique features that allow them to be distinguished from conventional meat (which involves the slaughter or otherwise demise of a live animal). The methods can also be tailored to achieve desired traits such as health benefits and sensory benefits. The points of distinction include at least the extended shelf life, levels of hormones, antibiotics, and microbial contamination in the cell-based meat, but can also include further customization such as altered levels of fat content, amino acid profiles, texture, and the like. These are considered in turn below.

A. Hormones

As compared to conventional meat, the slaughter-free cell-based meat of the disclosure comprises significantly lower amounts of steroid hormones. For example, using the culturing methods described, there need not be any exogenous hormones added into culture thus resulting in lower or non-existent hormonal levels in the resulting meat. Accordingly, in some embodiments, the slaughter-free cell-based meat product is substantially free of steroid hormones (i.e. contains little or no steroid hormones). This is in contrast to animals raised for conventional meat production, where they are often fed or otherwise administered exogenous hormones. It is noted that even animals (e.g. chicken, livestock) raised for conventional meat production that are not fed or administered any exogenous hormones, still have testosterone, estradiol, progesterone, among an array of others hormones, simply due to the basal production levels by the animals' glandular systems. Estradiol, progesterone, and testosterone are natural hormones found in conventional meat at some low level depending on animal gender. In contrast, the cell-based meat of the disclosure comprises lower levels of steroid hormones or is even substantially free of steroid hormones. For example, ELISA results for $17\beta$-estradiol indicated that slaughter-free chicken meat samples yielded a lower concentration compared to conventional chicken. $17\beta$-estradiol levels were on average 35 ng estradiol/kg wet mass for slaughter-free chicken meat using the ELISA kit whereas conventional chicken, procured from the local grocery, was 90 ng/kg estradiol/kg wet mass.

Accordingly, in some embodiments, the cell-based meat of the disclosure comprises no more than about 1 ug, 0.5 ug, 0.1 ug, 0.05 ug, 0.01 ug, 0.005 ug, or even about 0.001 ug steroid hormone/kg dry mass of cell-based meat. In some embodiments, the cell-based meat comprises no more than about 1 ug, 0.5 ug, 0.1 ug, 0.05 ug, 0.01 ug, 0.005 ug, or even about 0.001 ug progesterone/kg dry mass of cell-based meat. In some embodiments, the cell-based meat comprises no more than about 1 ug, 0.5 ug, 0.1 ug, 0.05 ug, 0.01 ug, 0.005 ug, or even about 0.001 ug testosterone/kg dry mass of cell-based meat. In some embodiments, the cell-based meat comprises no more than about 0.05 ug, 0.01 ug, 0.005 ug, or even about 0.001 ug estradiol/kg dry mass of cell-based meat. In exemplary embodiments, the cell-based meat comprises no more than about 35 ng estradiol/kg dry mass of cell-based meat.

B. Microbial Contamination

Using the culturing methods described, the slaughter-free cell-based meat product is substantially free of microbial contaminants. "Substantially free" means that the concentration of microbes or parasites is below a clinically significant level of contamination, e.g., below a level wherein ingestion would lead to disease or adverse health conditions. Such low levels of contamination leads to an increased shelf life. This is in contrast to animals raised for conventional meat production destined for slaughter. As used herein, microbial contamination includes, but is not limited to, bacteria, fungi, viruses, protozoa, and combinations thereof. Harmful microbes may include coliforms (fecal bacteria), *E. coli*, yeast, mold, *Campylobacter, Salmonella, Listeria*, and Staph. A skilled artisan would understand that any contaminant can be measured.

It is noted that the lower microbial contamination associated with the slaughter-free cell-based meat product of the disclosure as compared to conventional meat obtained by slaughter is exhibited at all temperatures: e.g. from about 0° C. to about 30° C., e.g. both at standard domestic refrigerator temperatures (e.g. about 2° C. to about 6° C.) and at room temperature (e.g. about 22° C. to about 25° C.). It is also noted that the lower microbial contamination associated with the slaughter-free cell-based meat product of the disclosure as compared to conventional meat obtained by slaughter is exhibited for at least 3 days, 7 days, 14 days, 30 days, or 148 days following harvest, is exhibited for at least about 1, 2, 3, 4, 5, 6, 7, 8, 9, 10, 11, 12, 13, 14, 15, 16, 17, 18, 19, 20, and more weeks following harvest. It is also noted that the lower contamination is observed both under aseptic conditions as well as under non-aseptic conditions, and the lower contamination is observed when the meat is measured post-harvest with no subsequent formulation, as well as when the meat is measured post-harvest, and post-formulation.

In addition, cells grown in culture may be substantially free from parasites such as tapeworms that infect cells of whole animals and that are transferred to humans through consumption of insufficiently cooked meat.

Aseptic techniques may also be employed in packaging the meat products as they come off the biological production line. Such quality assurance may be monitored by standard assays for microorganisms or chemicals that are already known in the art.

Figure 3:
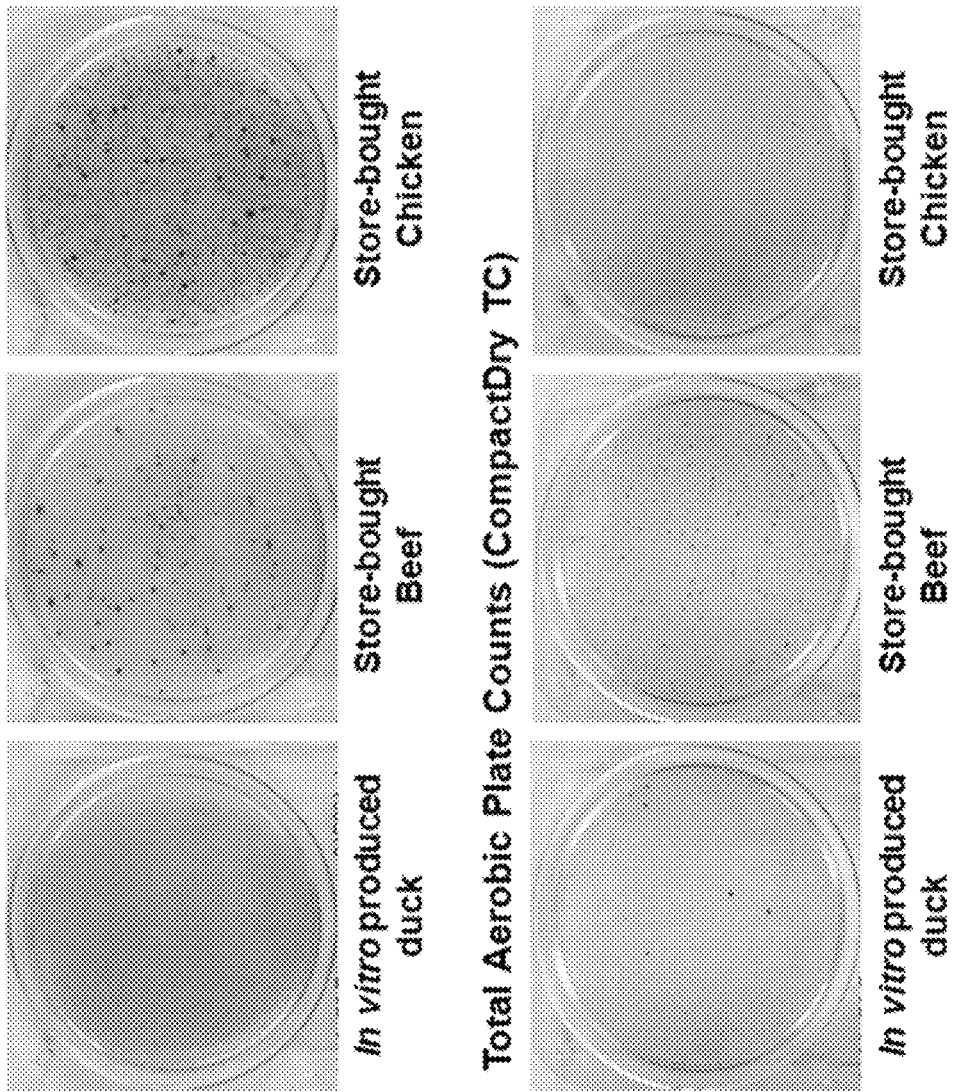
FIG. 3 shows representative plates with bacteria colonies, indicative of microbial contamination, showing results for exemplary samples of slaughter-free cell-based duck, store-bought (conventional) beef, and store-bought chicken.

As compared to conventional meat, the slaughter-free cell-based meat of the disclosure comprises a significantly lower amount of microbial contamination. Example 3, Example 9, Tables 12 and 13 provides a comparison of contaminants in the slaughter-free cell-based meat versus conventional grocery store meat obtained by slaughter. Conventional duck meat, and especially conventional beef, had significantly higher amounts of microbial contamination. FIG. 3 shows representative plates indicating bacteria colonies, specifically showing results for cell-based duck, conventional beef, and conventional chicken.

Accordingly, in some embodiments, provided herein is a slaughter-free meat product for dietary consumption exhibiting a lower microbial contamination count as compared to conventional meat obtained by slaughter, wherein the lower microbial contamination count is exhibited for at least 3 days following harvest.

In some embodiments, the lower microbial contamination count is exhibited at least 2, 3, 4, 5, 6, 7, 10, 14, 15, 20, 21, 25, 30, 40, 50, 60, 70, 80, 90, 100, 110, 120, 130, 140, 148, 150, 160, 170, 180, 190, 200, 210, 220, 230, 240, or at least 250 days following harvest.

In some embodiments, the microbial contamination count is determined following harvest, and prior to formulation. In other embodiments, the microbial contamination count is determined following formulation.

In some embodiments, the slaughter-free meat product is maintained under non-aseptic conditions and still exhibits the lower microbial contamination counts.

In some embodiments the microbial contamination count is determined by measuring the total microbial count (TC), *E. coli*/coliform count (EC), *E. coli* microbial count, the coliforms count, or the *E. coli*/coliforms count. In some embodiments the microbial contamination count is determined by measuring the count for other microbe including, but not limited to mold, yeast, *Salmonella, Listeria*, and staph.

In some embodiments the slaughter-free meat product comprises:

(a) no more than 100 cfus microbial contamination/g wet mass determined as per the FDA bacteriological analytical manual;

(b) no more than 10 cfus coliform contamination/g wet mass determined as per the FDA bacteriological analytical manual;

(c) no more than 10 cfus *E. coli* contamination/g wet mass determined as per the FDA bacteriological analytical manual;

(d) no more than 10 cfus yeast contamination/g wet mass determined as per the FDA bacteriological analytical manual;

(e) no more than 10 cfus mold contamination/g wet mass determined as per the FDA bacteriological analytical manual;

(f) no detectable level of *Salmonella* contamination/25 g wet mass determined as per the FDA bacteriological analytical manual;

(g) no detectable level of *Listeria* contamination/25 g wet mass determined as per the AOAC 2004.06 method;

(h) no more than 10 cfus Staph contamination/g wet mass determined as per the AOAC 2003.07 method; and/or (i) no more than 55 cfus total aerobic count contamination/g wet mass determined as per the CompactDry protocol.

In some embodiments, the slaughter-free meat product comprises slaughter-free chicken, duck, or bovine meat, and the conventional meat comprises chicken, duck or bovine meat obtained by slaughter.

Examples 3 and 9 provide a variety of exemplary protocols under which the shelf life and microbial contamination is observed. A skilled artisan would understand that there are a number of methods by which to measure microbial contamination. These are provided at least by the following texts: (1) FDA Bacteriological Analytical Manual (BAM) (Edition 8, Revision A/1998) and (2) USDA Food Safety and Inspection Service Microbiology Laboratory Guidebook. The AOAC also provides at least the following tests for determination of microbial contamination:

a. Enterobacteriaceae, AOAC 2003.01
  b. *E. coli* and coliforms, AOAC 998.08
  c. Yeast and mold, FDA BAM Ch. 18
  d. *Listeria*, AOAC 2004.06
  e. *Salmonella* (25 g), AOAC 2011.03
  f. *Campylobacter*, AOAC RI 051201
  g. AOAC 2003.07—Staph
  h. Aerobic plate counts, AOAC 990.12
  i. *Salmonella*, AOAC 2013.02, RI PTM 081201
  j. *Listeria* species, AOAC-RI PTM #081401
  k. Aerobic Count, AOAC 990.12 l. Coliforms & *E. coli*, AOAC 991.14 m. Y&M Count, AOAC 2014.05

C. Antibiotics

As compared to conventional meat, the slaughter-free cell-based meat of the disclosure comprises significantly lower amounts of antibiotics, or is substantially free of antibiotics, or is free of antibiotics entirely. For example using the culturing methods described, the use of antibiotics in culture can be controlled or eliminated, thus resulting in lower or non-existent antibiotic levels in the resulting cell-based meat. Accordingly, in some embodiments, the slaughter-free cell-based meat product is substantially free of antibiotics (i.e. contains little or no antibiotics). This is in contrast to animals raised for conventional meat production, where they are often fed or otherwise administered exogenous antibiotics.

Accordingly, in some embodiments, the cell-based meat of the disclosure comprises no more than about 100 ug antibiotics/kg dry mass of cell-based meat, 90 ug antibiotics/kg dry mass of cell-based meat, 80 ug antibiotics/kg dry mass of cell-based meat, 70 ug antibiotics/kg dry mass of cell-based meat, 60 ug antibiotics/kg dry mass of cell-based meat, 50 ug antibiotics/kg dry mass of cell-based meat, 40 ug antibiotics/kg dry mass of cell-based meat, 30 ug antibiotics/kg dry mass of cell-based meat, 20 ug antibiotics/kg dry mass of cell-based meat, 10 ug antibiotics/kg dry mass of cell-based meat, 5 ug antibiotics/kg dry mass of cell-based meat, 1 ug antibiotics/kg dry mass of cell-based meat, 0.5 ug antibiotics/kg dry mass of cell-based meat, 0.1 ug antibiotics/kg dry mass of cell-based meat, 0.05 ug antibiotics/kg dry mass of cell-based meat, or even about 0.01 ug/kg of antibiotics/kg dry mass of cell-based meat.

D. Lipids

As compared to conventional meat, the slaughter-free cell-based meat of the disclosure comprises a lower average total lipid (fat) content. Cell-based meat generally has an average total fat content between about 0.5% to about 5.0%, whereas the fatty acid content in conventional meat varies widely and can range from about 3% to about 18%, depending on the cut of meat.

Figure 4:
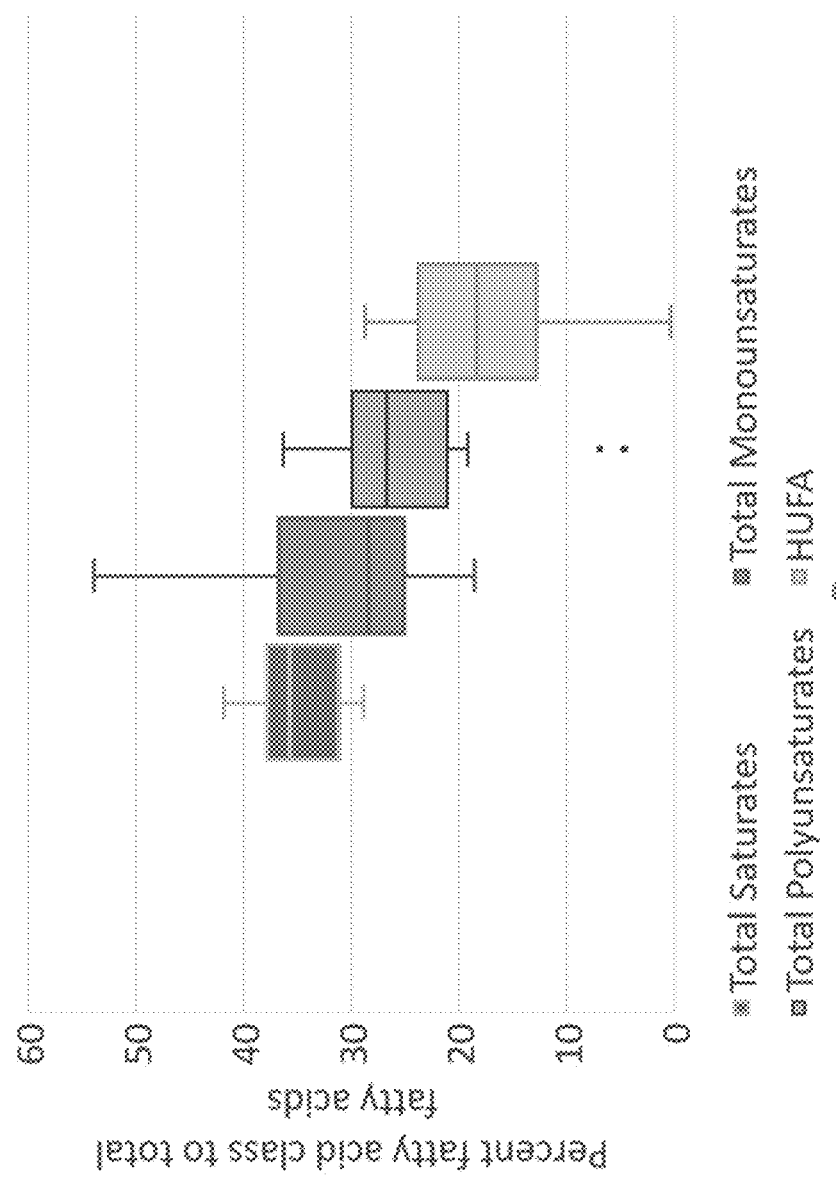
FIG. 4 shows total fatty acid composition for saturated, monounsaturated and polyunsaturated fatty acids across exemplary of slaughter-free cell-based meat samples.

Table 14 shows the total fatty acid analysis for several exemplary slaughter-free cell-based meat samples. FIG. 4 shows total fatty acid composition for saturated, monounsaturated and polyunsaturated fatty acid across exemplary slaughter-free cell-based meat samples.

Accordingly, in some embodiments, the cell-based meat of the disclosure comprises an average total fat content of about 0.5%, about 0.6%, about 0.7%, about 0.8%, about 0.9%, about 1.0%, about 1.1%, about 1.2%, about 1.3%, about 1.4%, about 1.5%, about 1.6%, about 1.7%, about 1.8%, about 1.9%, about 2.0%, about 2.1%, about 2.2%, about 2.3%, about 2.4%, about 2.5%, about 2.6%, about 2.7%, about 2.8%, about 2.9%, about 3.0%, about 3.1%, about 3.2%, about 3.3%, about 3.4%, about 3.5%, about 3.6%, about 3.7%, about 3.8%, about 3.9%, about 4.0%, about 4.1%, about 4.2%, about 4.3%, about 4.4%, about 4.5%, about 4.6%, about 4.7%, about 4.8%, about 4.9%, or about 5.0%, when measured as a % of total wet mass of the cell-based meat.

In some exemplary embodiments, the cell-based meat comprises one or more of the following fatty acids classes in the amounts indicated, expressed as % of that class over total fatty acids:

a. saturated fatty acids content between about 10% to about 60%, e.g. about 20% to about 50%, about 30% to about 40%, about 10% to about 50%, about 10% to about 40%, about 10% to about 30%, and/or about 10% to about 20%.

b. monounsaturated fatty acids content between about 10% to about 60%, e.g. about 20% to about 50%, about 30% to about 40%, about 10% to about 50%, about 10% to about 40%, about 10% to about 30%, and/or about 10% to about 20%.

c. polyunsaturated fatty acids content between about 1% to about 50%, e.g. about 10% to about 40%, about 20% to about 30%, about 30% to about 20%, and/or about 40% to about 10%.

In some embodiments, the cell-based meat of the disclosure comprises a ratio of about 2:1 to about 18:1 of omega 6:3 fatty acids classes. (α-linolenic acid (ALA), eicosapentaenoic acid (EPA) and docosahexaenoic acid (DHA) are major omega 3 fatty acids). Accordingly, in some embodiments, the cell-based meat of the disclosure comprises a ratio of about 2:1, 3:1, 4:1, 5:1, 6:1, 7:1, 8:1, 9:1, 10:1, 11:1, 12:1, 13:1, 14:1, 15:1, 16:1, 17:1, or about 18:1 of omega 6:3 fatty acids classes. On the other hand, conventional meat, e.g. conventional chicken comprises a ratio of >18:1 omega 6:3 fatty acids classes.

The lower fat content of cell-based meat provides a lower caloric content, lower omega 6:3 ratios, as well as other related health benefits, when compared to conventional meat.

The slaughter-free cell-based meat production can further be customized to achieve desired profiles. Post-harvest desiccation can further increase the fat content and/or other solid components. Increasing lipid content in the growth medium can increase the fat content as well.

The flavor and aroma of the cell-based meat of the disclosure can be altered during the production. Generally, the higher proportion of unsaturated fatty acids in the meat gives more unsaturated volatile aldehydes and such compounds may be important in determining the specific aromas of these species.

Figure 7:
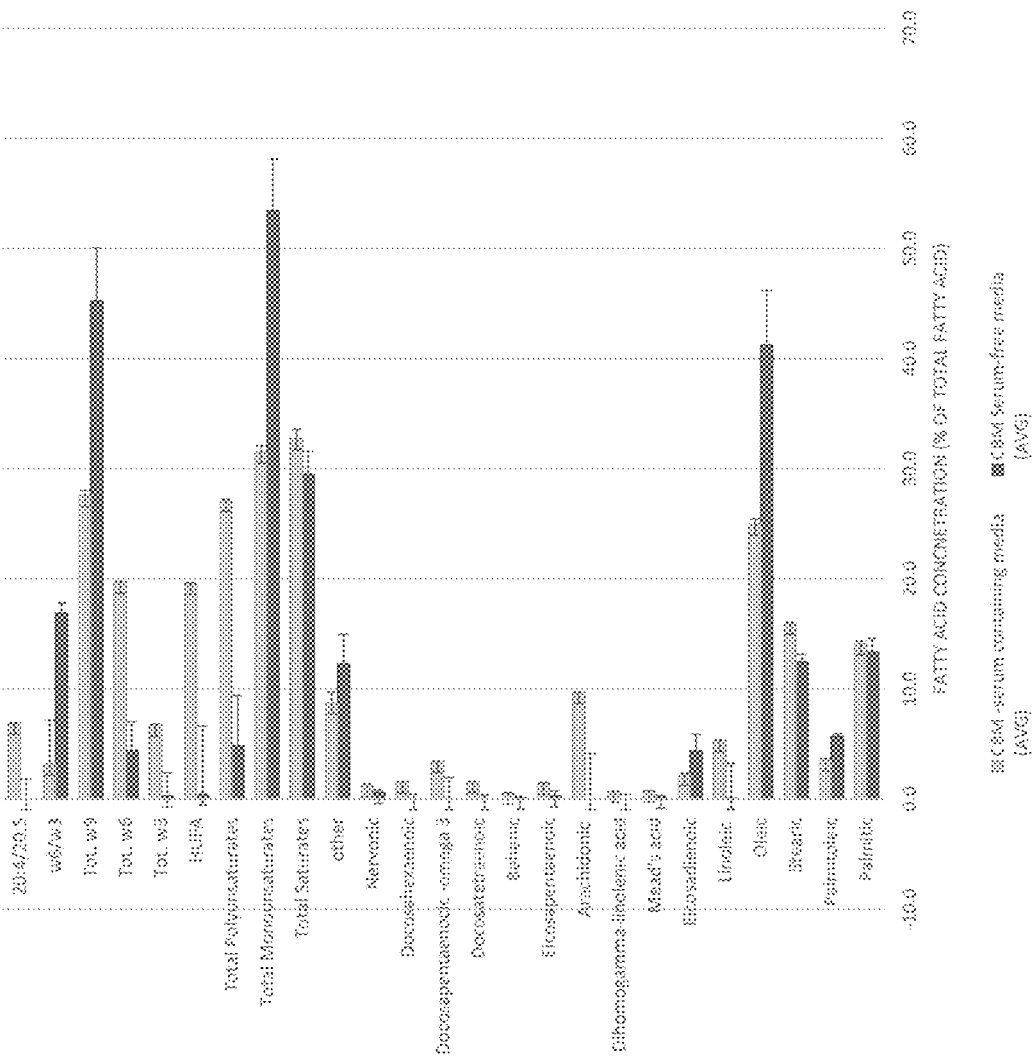
FIG. 7 shows that the presence of serum in the media used to generate cell-based meat (CBM) from cells in culture can affect fatty acid profiles; the figure shows the fatty acid percentages in exemplary slaughter-free cell-based meat samples, produced in serum free media vs. media containing serum. W3=omega 3 FA; W=6=omega 6 FA; W=9=omega 9 FA.
Figure 8:
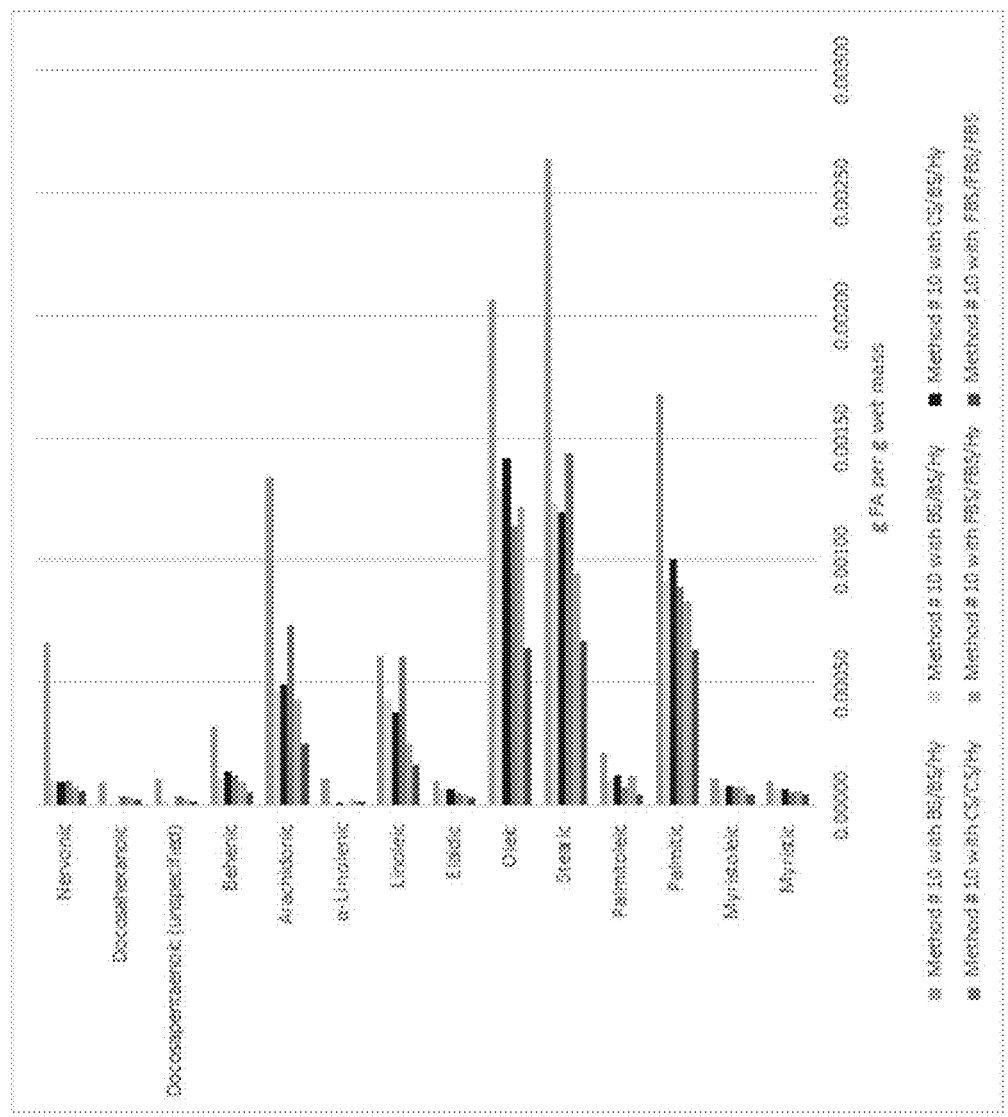
FIG. 8 shows that using serum from different sources imparts different fatty acid profiles in slaughter-free cell-based meat samples. The data are from Method 10 from Table 1. Key—BS: Bovine serum; CS: Chicken serum; FBS: Fetal bovine serum; Hy: soy-based plant hydrolysate; Media contained 8-10% of particular serum; DMEM-F12 was used as the base media.
Figure 10:
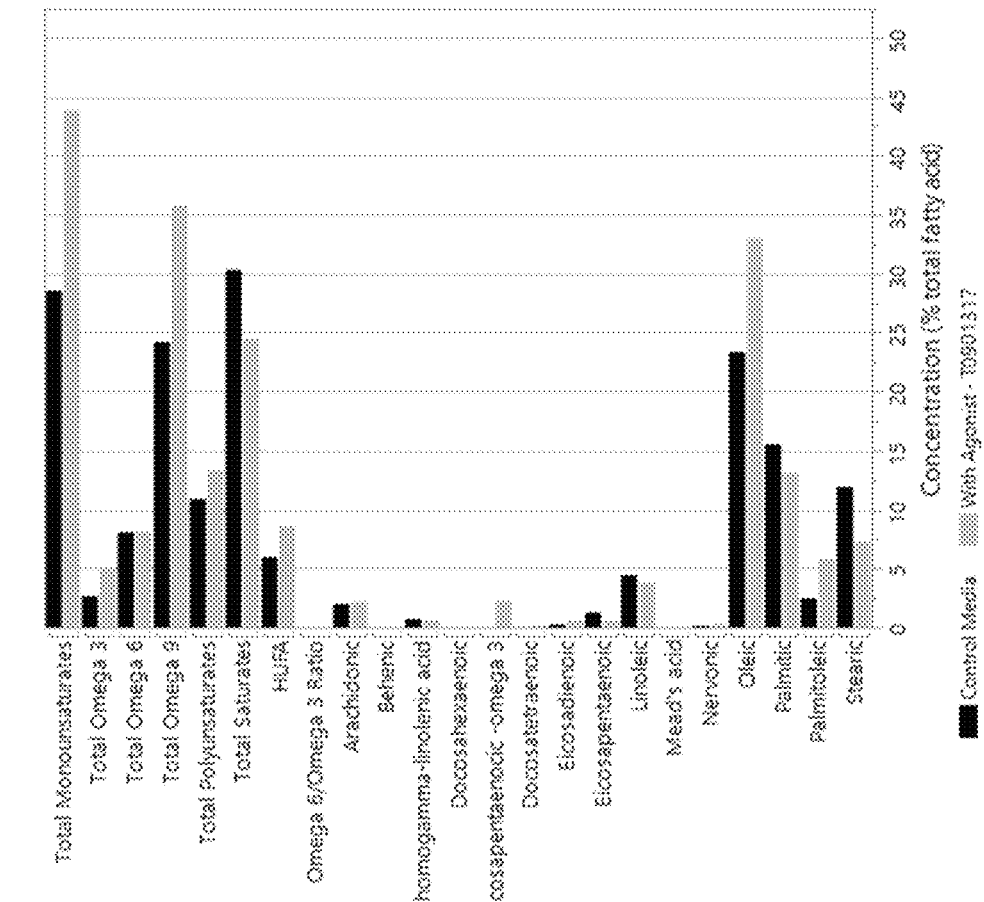
FIG. 10 shows that fatty acid profiles of slaughter-free cell-based meat are affected by media composition, and the addition of an agonist that targets the Liver X Receptor β (LXRβ).
Figure 11:
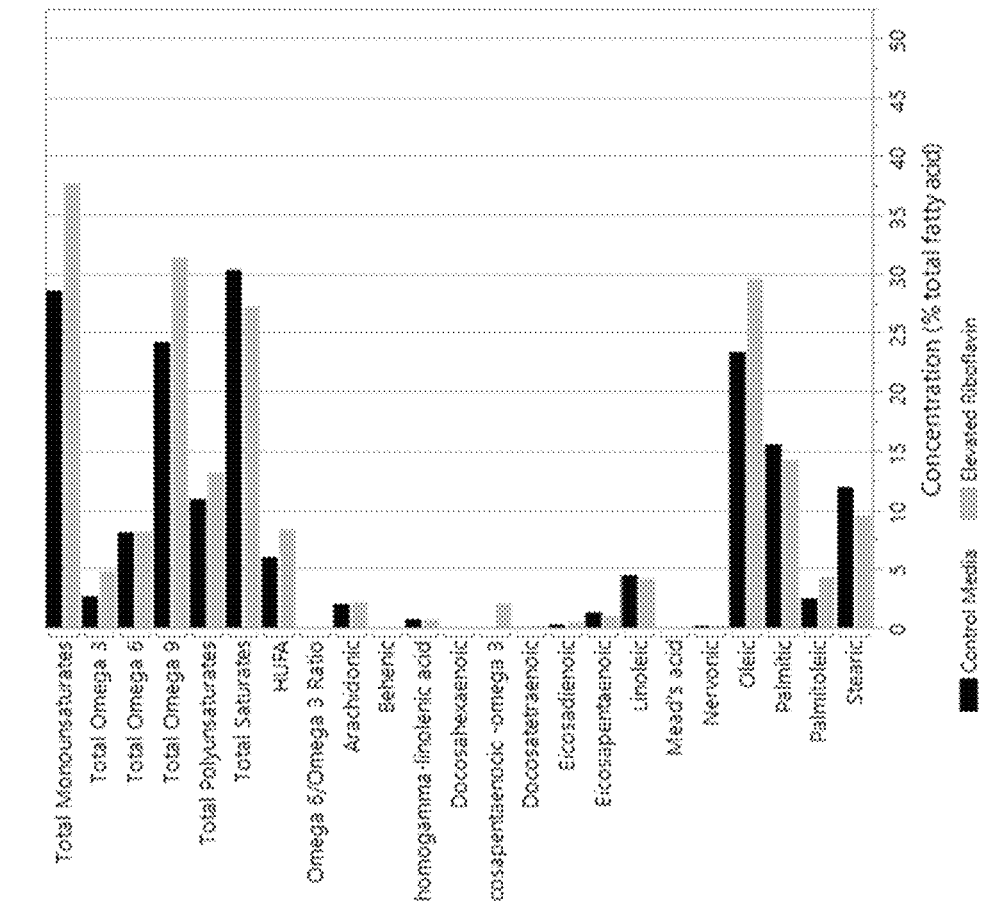
FIG. 11 shows that fatty acid profiles of slaughter-free cell-based meat are affected by media composition, and the addition of riboflavin.

Accordingly, the methods provided herein can alter specific fatty acid profiles to achieve desired flavor characteristics or fatty acid profiles such as Omega 3:6 ratio through at least the following mechanisms:

a. In some embodiments, the presence of serum in the media can affect fatty acid profiles. FIG. 7 shows the fatty acid percentages in serum free media vs. media containing serum.

b. In some embodiments, serum of different sources can be used in culture to achieve different fatty acid profiles in the slaughter-free cell-based meat product. (FIG. 8)

c. In some embodiments, the use of isolated clones from a polyclonal population can be used to alter fatty acid profiles as well. (FIG. 9).

d. In some embodiments, the fatty acids profiles are modulated by altering the media's fatty acid composition or by the addition of media components including compounds added to change fatty acid composition such as, but not limited to an agonist (e.g. an agonist of LXRβ), or riboflavin. Such adjustments to media can impact fat profiles. (FIG. 10, FIG. 11).

e. In some embodiments, the fatty acid profiles are modulated by the composition of the cells in culture. Accordingly, in some embodiments, the fibroblasts in culture, the myoblasts in culture, or the fibroblasts/myoblasts in co-culture can be further modified to include adipocytes.

Figure 9:
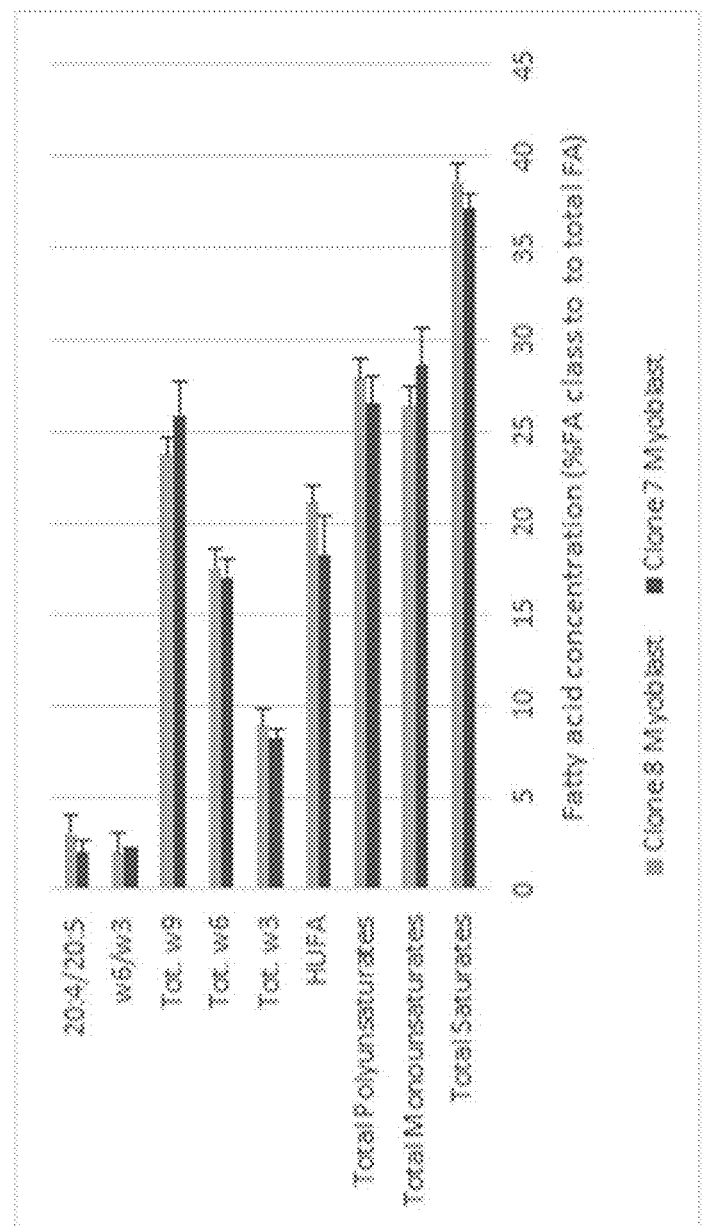
FIG. 9 shows that isolated clones of myoblast cells from a polyclonal population of myoblast cells can impact the fatty acid profile of slaughter-free cell-based meat samples.

In FIG. 9, tissue (cell sheets) were formed using a co-culture method (described in the Method 15 in Table 1)

using culture media with enhanced levels of various compounds to modulate specific biochemical pathways. Riboflavin, a vitamin and common co-factor, was titrated into cell culture media. The global effect on fatty acid concentrations are shown.

The lower levels of fatty acids in the cell-based meat of the disclosure also promote an extended shelf life of the meat, for example by leading to lower levels of fatty acid oxidation products in the meat.

E. Amino Acids

It is also desirable that the slaughter-free cell-based meat product of the disclosure shares similarities with conventional meat products. The slaughter-free cell-based meat product of the disclosure generally comprises about 50 g to about 95 g by weight of amino acids per 100 g dry mass. For example, the cell-based meat of the disclosure comprises one or more of the following amino acids in the indicated amounts (the amounts expressed as g of amino acid/100 g total amino acid): Tryptophan about 1 to about 2.2, Threonine about 4.6 and 6.5, Isoleucine about 3.8 to about 5, Leucine about 6.1 to about 8.9, Lysine about 5.7 to about 8.8, Methionine about 0.14 to about 3.0, Cysteine about 1.5 to about 1.8, Phenylalanine about 3.7 to about 4.8, Tyrosine about 3.0 to about 5.2, Valine about 4.8 to about 6.1, Arginine about 7.0 to about 8.0, Histidine about 2.5 to about 4, Alanine about 5.0 to about 6.3, Aspartic acid about 8.6 to about 10.4, Glutamic acid about 12.5 to about 14.6, Glycine about 4.6 to about 9.8, Proline about 4.6 to about 6.8, Serine 4.4 to 5.3, and/or Hydroxyproline about 0.0 to 4.0.

In some embodiments, hydroxyproline levels are elevated in the cell-based meat generated from fibroblast monocultures, as compared to the conventional counterpart. Without being held to any theory or mechanism, such an increase in the hydroxyproline levels may be due higher levels of collagen formation resulting from the secretion of extracellular matrix components by fibroblast cells. In some embodiments, when myoblasts (MB) are added to the culture system either as a polyclonal cell mixture (mixed population of myoblasts) or monoclonal myoblast cell mixture (single-cell isolated from a mixed population and expanded), the hydroxyproline concentration can be reduced to close to that of conventional meat. It is noted that in the embodiments provided herein the hydroxyproline concentration may also be modulated to alter the texture of the meat product.

F. Vitamin E Content

As compared to conventional meat, the slaughter-free cell-based meat of the disclosure comprises a higher Vitamin E ($\alpha$-Tocopherol) content. In some embodiments, the slaughter-free cell-based meat product of the disclosure comprises at least about 0.5 mg, at least about 0.6 mg, at least about 0.7 mg, at least about 0.8 mg, at least about 0.9 mg, or at least about 1.0 mg/Vitamin E/100 g wet mass of cell-based meat.

G. Moisture Content

The slaughter-free cell-based meat product the disclosure generally has a moisture content of about 65% to about 95%. In some embodiments, the moisture content is measured after harvesting, but before formulation. In other embodiments, the moisture content is measured after formulation.

H. Architecture of Cell-Based Meat

There are additional points of distinction between slaughter-free cell-based meat and conventional meat. While it is not required for cells grown purely for meat purposes (as described herein) to possess functional characteristics that would allow for transplantation and function, under some circumstances they may be further engineered to include components that would confer functionality.

Cell-based meat, unless otherwise manipulated to include, does not include vascular tissues, such as veins and arteries, whereas conventional meat does contain such vasculature, and contains the blood found in the vasculature. Accordingly, in some embodiments, the cell-based meat is substantially free of any vasculature. As generally contemplated herein, vasculature includes blood and/or lymphatic fluid.

Likewise, cell-based meat, although composed of muscle or muscle-like tissues, unless otherwise manipulated to include, does not comprise functioning muscle tissue. Accordingly, in some embodiments, the cell-based meat does not comprise functioning muscle tissue.

It is noted that features such as vasculature (that may contain blood, lymph, etc.) and functional muscle tissue can be further engineered into the cell-based meat, should there be a desire to do so. For example, protocols that lead to sprouting of vessels may be utilized to introduce vasculature into the slaughter-free meat products of the disclosure, and allow for increased perfusion to the meat product.

I. Flavor

The fatty acid composition of meat generally impacts the overall meat quality and influences flavor, juiciness, and tenderness of the meat (Wood et al., Manipulating meat quality and composition. Proceedings of the Nutrition Society. 1999; 58:363-370. DOI: org/10.1017/5009665199000488). Specific fatty acids, such MUFA oleic acid (18:1 $\omega$9) and MUFA palmitoleic acid (16:1 $\omega$9) are fatty acids that are often primarily associated with good flavor.

Fattier meat is generally tastier, but with greater fat content comes greater risk of adverse Fat profiles in meat drive key organoleptic profiles that not only drive consumer preferences, but also establish unique species identification. However, certain fat types are associated with a greater risk of adverse health consequences such as heart disease. Thus, overall cell culture media composition, fatty acid supplementation into the culture, and/or the ratio of myoblasts/fibroblasts/adipocytes/endothelial cells/other cells mesodermal lineage may be regulated in culture to produce the slaughter-free cell-based meat products with optimal flavor and health effects. In exemplary embodiments, the ratio of adipocytes is altered in the co-culture. Regulation may be achieved by selecting specific clones of myogenic cells, controlling the ratio of the cells that are initially seeded in culture, and/or by varying, as desired, the concentrations and ratio of growth factors or other media components that act upon the cells. Specific fatty acids, like MUFA oleic acid (18:1 $\omega$9), can be enriched through media composition and nutritional design.

J. Supplementation

In other embodiments, other nutrients such as vitamins may be added to increase the nutritional value of the meat. For example, this may be achieved through the exogenous addition of the nutrients to the growth medium or through genetic engineering techniques.

K. Cooked Bite Force and Hardness

Figure 13:
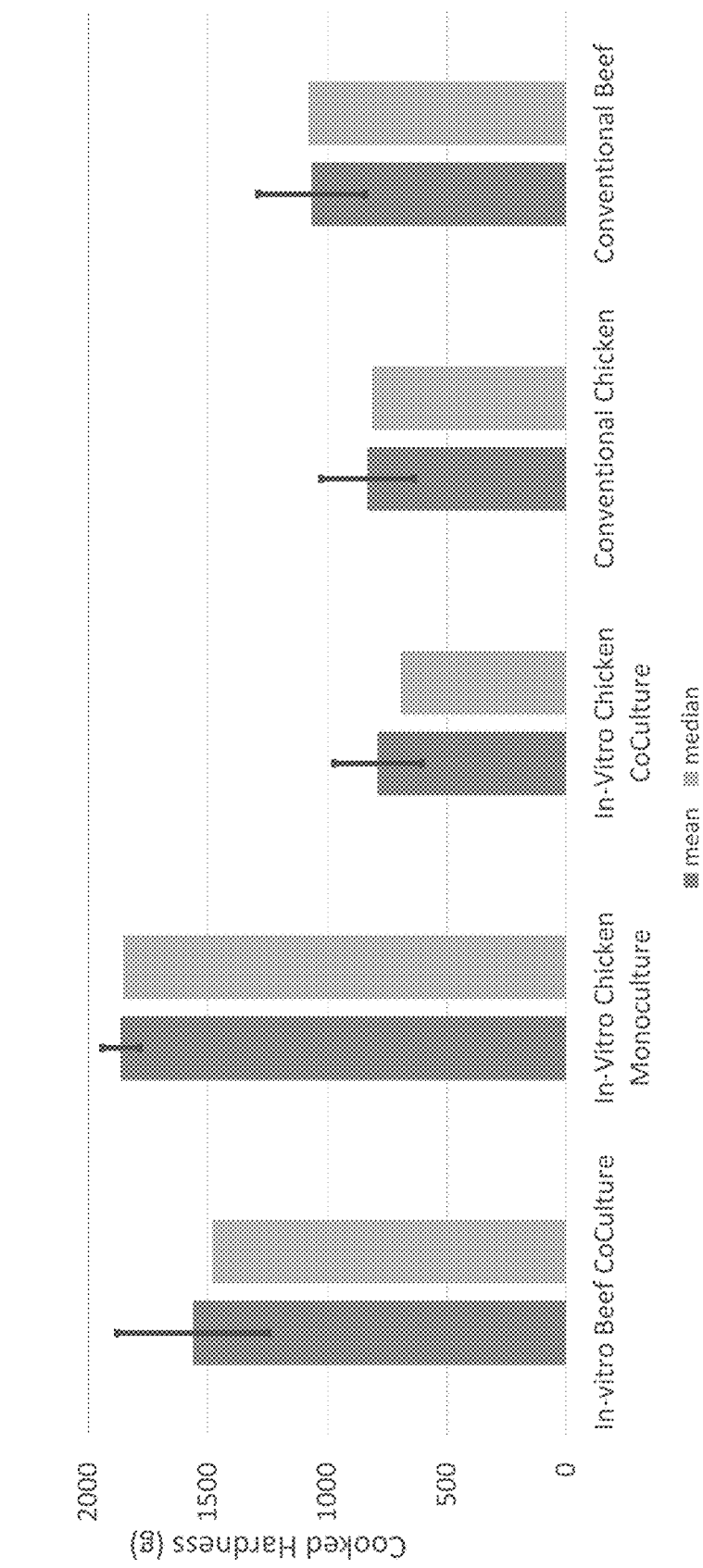
FIG. 13 shows the cooked hardness of slaughter-free cell-based meat generated from fibroblast/myoblast co-cultures, and monocultures, as compared to conventional chicken and beef.

The slaughter-free slaughter-free cell-based meat product of the disclosure can be modified to achieve certain textual features, such as a desired cooked bite force or cooked hardness. Table 17 shows the cooked texture of exemplary cell-based meat samples. FIG. 13 shows the cooked hardness of exemplary meat generated from cells in either myoblast:fibroblast co-culture or fibroblast monoculture.

The cooked bite force of a cell-based meat of the disclosure can range from about 100 g to 5000 g. In some exemplary embodiments, the cooked bite force of a cell-based meat of the disclosure, as harvested from adherent cells in culture, ranges from about 450 g to about 3000 g. In some embodiments, the cooked hardness of a cell-based meat of the disclosure as harvested from adherent cells in culture, ranges from about 2500 g to about 2000 g. In some embodiments the cooked bite force and/or cooked hardness of a cell-based meat of the disclosure is at or below the detection limit, e.g. in some embodiments where the meat is harvested from cells grown in a suspension culture.

L. Shelf Life

A significant portion of meat and meat products are spoiled every year. It is estimated that approximately 3.5 billion kg of poultry and meat are wasted at the consumer, retailer, and foodservice levels which have a substantial economic and environmental impact (Kantor et al. (1997)). A significant portion of this loss is due to microbial spoilage.

Conventional meat is perishable and has a relatively short shelf life stability (interchangeably referred to as simply "shelf life" herein). The composition of conventional meat and the conditions used to slaughter and harvest the meat generally create favorable growth conditions for various microorganisms including fecal bacteria (e.g. coliform bacteria); conventional meat is also very susceptible to spoilage due to chemical, oxidative, and enzymatic activities. Accordingly, as used herein, in some embodiments, the shelf life is the amount of time a food remains fit for dietary consumption while still being palatable, e.g. not causing any disease or adverse health effects, such as vomiting, diarrhea, nausea, and the like upon ingestion, and not producing an aroma that would suggest that the process of decay (e.g. microbially-induced, molecular decay, physical decay) has begun.

Without being bound by theory or mechanism, it is generally regarded that microbial growth, oxidation, and enzymatic autolysis are three mechanisms responsible for the spoilage of meat, thereby reducing the shelf life. The breakdown of fat, protein, and carbohydrates of meat results in the development of off-odors and off-flavor and these the off-odors and off-flavors make the meat objectionable for human consumption. Depending on the species and method of harvest, conventional meat products are not safe to consume after a relatively short period of storage time. For example, chicken should be cooked within a few days of purchasing. Cooked poultry can be safely stored in the refrigerator for about only 3-5 days and the freezer for up to about 3-5 months. It is, therefore, necessary to control meat spoilage in order to increase its shelf life and maintain its nutritional value, texture and flavor.

The shelf life of conventional meat is often increased by various processes including adding preservatives, pickling, salting, dehydrating, canning, fermenting, or storing in darkness. The cell-based meat of the disclosure exhibits extended shelf life, without the use of any of these methods, but it is noted that such methods could be added to even further enhance the shelf life. Accordingly in some embodiments, the cell-based meat of the disclosure exhibits a measurement indicative of an increase in shelf life, as compared to conventional meat obtained by slaughter, where the conventional meat is unprocessed (e.g. no process has been further applied, such as those listed above).

Slaughter-free cell-based meat, through its method of production and composition, produces a meat product that has extended shelf life compared to conventional meat products and does not require the addition of preservative agents to obtain the shelf life stability. The composition of cell-based meat is such that fewer off-odors and off-flavors are detected. In addition, the manufacturing methods used to produce cell-based meat require clean and aseptic conditions. These conditions ensure that microbial cell counts in both harvested products and subsequent food processing are low. These multiple factors contribute to extended shelf life stability of cell-based meat The shelf life due to spoilage of the cell-based meat of the disclosure is enhanced relative to conventional meat. This is the case both at all temperatures, e.g. at room temperature (about 22° C. to about 26° C.) and at colder temperatures akin to domestic refrigerator temperatures (e.g. at about 2° C. to about 4° C.). The extended shelf life is associated with reduced contamination, composition of the cell-based meat, reduced degradation of the cell-based meat and slower rates of change in color, spoilage, smell and flavor of the cell-based meat, and allows the meat to be maintained for dietary consumption.

Without being bound to theory or mechanism, there is a decrease in total fatty acid content in the cell-based meat, as compared to conventional meat, resulting in lower levels of fatty acid oxidation products, leading to slower rates of change in the color, smell, or flavor of the meat. Oxidative rancidity is associated with the degradation by oxygen in the air. The double bonds of an unsaturated fatty acid can be cleaved by free-radical reactions involving molecular oxygen. This reaction causes the release of malodorous and highly volatile aldehydes and ketones. Oxidation primarily occurs with unsaturated fats. For example, even though meat is held under refrigeration or in a frozen state, the polyunsaturated fat can continue to oxidize and slowly become rancid. The fat oxidation process begins immediately after the animal is slaughtered and the muscle, intra-muscular, inter-muscular, and surface fat becomes exposed to oxygen of the air.

Without being bound to theory or mechanism, there is a decrease the number of lipases in the cell-based meat, as compared to conventional meat, resulting in lower levels of fatty acid breakdown, leading to slower rates of change in the color, smell, or flavor of the meat.

Without being bound to theory or mechanism, due to the absence of vasculature in the cell-based meat, when compared to conventional meat, there is less oxygen present, resulting in lower levels of fatty acid oxidation and growth of aerobic bacteria, leading to reduced microbial contamination levels, and leading to slower rates of change in the color, smell, aroma or flavor of the meat.

Without being bound to theory or mechanism, due to the absence of functional muscle tissue (e.g. myoglobin) in the cell-based meat when compared to conventional meat, there is less oxygen present, resulting in lower levels fatty acid oxidation and the growth of aerobic bacteria, leading to reduced microbial contamination levels, and leading to slower rates of change in the color, smell, or flavor of the meat.

Without being bound to theory or mechanism, due to higher amounts of Vitamin E in the cell-based meat when compared to conventional meat, there are higher levels of antioxidant activity, resulting in protection against fatty acid oxidation, and leading to slower rates of change in the color, smell, or flavor of the meat. Oxidation of lipids in meat depends on several factors including fatty acid composition, the level of the antioxidant vitamin E (α-tocopherol), and prooxidants such as the free iron presence in muscles.

Accordingly, in some embodiments, as compared to conventional meat, the shelf life of slaughter-free cell-based meat product is extended by at least about 1.5×, at least about 2×, at least about 2.5×, at least about 3×, at least about 3.5×, at least about 4×, at least about 4.5×, at least about 5×, at least about 5.5×, at least about 6×, at least about 6.5×, at least about 7×, at least about 7.5×, at least about 8×, at least about 8.5×, at least about 9×, at least about 9.5×, or even at least about 10×. The shelf life increases are observed both at about 2° C., and about 26° C., and all temperatures in between, inclusive of the endpoints.

In some embodiments, provided herein is a slaughter-free cell-based meat product for dietary consumption exhibiting an extended shelf life, wherein the shelf life is extended compared to conventional meat obtained by slaughter, and wherein the shelf life is extended at all temperatures. In some embodiments the extended shelf life is maintained for at least 2, 3, 4, 5, 6, 7, 10, 14, 15, 20, 21, 25, 30, 40, 50, 60, 70, 80, 90, 100, 110, 120, 130, 140, 148, 150, 160, 170, 180, 190, 200, 210, 220, 230, 240, or at least 250 days following harvest. In some embodiments the extended shelf life is maintained for at least 3, 7, 14, 30, or 148 days following harvest at about 22° C.-26° C. In some embodiments the shelf life is determined after harvest, and prior to formulation. In some embodiments the shelf life is determined after formulation. In some embodiments the shelf life is extended under non-aseptic conditions, both at about 2° C. to about 6° C., and at about 22° C.-26° C. In some embodiments the shelf life is determined by measuring the total microbial count (TC), for *E. coli*/coliforms (EC), *E. coli* microbial count, or the coliforms count.

In some embodiments the TC measurement of conventional meat obtained by slaughter is at least 1.5×, 2×, 2.5×, 3×, 3.5×, 4×, 4.5×, 5×, 10×, 15×, 20×, or even 25× higher than that of the TC measurement of slaughter-free meat product, and leads to its lower shelf life.

In some exemplary embodiments the slaughter-free cell-based meat product comprises one or more of the following features, which in part contributes to the exhibited extended shelf life:
  (a) no detectable level or no more than 1, 10, 50, or 100 cfus microbial contamination/g wet mass determined as per the FDA bacteriological analytical manual;
  (b) no detectable level or no more than 1, 10, 50, or 100 cfus coliform contamination/g wet mass determined as per the FDA bacteriological analytical manual;
  (c) no detectable level or no more than 1, 10, 50, or 100 cfus *E. coli* contamination/g wet mass determined as per the FDA bacteriological analytical manual;
  (d) no detectable level or no more than 1, 10, 50, or 100 cfus yeast contamination/g wet mass determined as per the FDA bacteriological analytical manual;
  (e) no detectable level or no more than 1, 10, 50, or 100 cfus mold contamination/g wet mass determined as per the FDA bacteriological analytical manual;
  (f) no detectable level or no more than 1, 10, 50, or 100 cfus of *Salmonella* contamination/g wet mass determined as per the FDA bacteriological analytical manual;
  (g) no detectable level of or no more than 1, 10, 50, or 100 cfus *Listeria* contamination/g wet mass determined as per the AOAC 2004.06 method;
  (h) no detectable level of or no more than 1, 10, 50, or 100 cfus Staph contamination/g wet mass determined as per the AOAC 2003.07 method; and/or
  (i) no detectable level of or no more than 1, 10, 50, or 100 cfus no more than 55 cfus total aerobic count contamination/g wet mass determined as per the CompactDry protocol.

In some embodiments the slaughter-free meat product exhibiting the extended shelf life comprises slaughter-free chicken, duck, or bovine meat, and the conventional meat comprises chicken, duck or bovine meat obtained by slaughter.

Example 9 discusses a variety of exemplary protocols under which the shelf life and microbial contamination is observed. A skilled artisan would understand that there are a number of methods by which to measure shelf life, and parameters associated with shelf life, such as microbial contamination. These are provided at least by the following texts: (1) FDA Bacteriological Analytical Manual (BAM) (Edition 8, Revision A/1998) and (2) USDA Food Safety and Inspection Service Microbiology Laboratory Guidebook. The AOAC also provides at least the following tests for determination of microbial contamination:
  a) Enterobacteriaceae, AOAC 2003.01
  b) *E. coli* and coliforms, AOAC 998.08
  c) Yeast and mold, FDA BAM Ch. 18
  d) *Listeria*, AOAC 2004.06
  e) *Salmonella* (25 g), AOAC 2011.03
  f) *Campylobacter*, AOAC RI 051201
  g) AOAC 2003.07—Staph
  h) Aerobic plate counts, AOAC 990.12
  i) *Salmonella*, AOAC 2013.02, RI PTM 081201
  j) *Listeria* species, AOAC-RI PTM #081401
  k) Aerobic Count, AOAC 990.12
  l) Coliforms & *E. coli*, AOAC 991.14
  m) Y&M Count, AOAC 2014.05

Additional endpoints may be tested as indicative of shelf life. These include but are not limited to: rancidity testing; accelerated shelf life study; moisture, pH and water activity variability; product stability under varying storage conditions; microbiological, chemical and physical testing; sensory evaluation; and probiotic stability.

III. ENUMERATED EMBODIMENTS

Set 1

Embodiment 1. A cell-based meat product, wherein the cell-based meat product comprises at least two of the following features:
  a. no more than about 1 ug steroid hormone/kg dry mass cell-based meat product;
  b. no more than about 100 ug antibiotics/kg dry mass cell-based meat product;
  c. no more than about 100 cfus microbial contamination/g wet mass of cell-based meat product;
  d. an average total fat content between about 0.5% to about 5.0% when measured as % of wet mass of cell-based meat product;
  e. is substantially free of vasculature; and
  f. has at least a 2× increase in shelf life as compared to conventional meat.

Embodiment 2. The cell-based meat product of embodiment 1, wherein the cell-based meat product comprises at least, three, four, five, or six of the features (a) to (f).

Embodiment 3. The cell-based meat product of embodiments 1 to 2, wherein the cell-based meat product comprises no more than about 1 ug progesterone/kg dry mass of cell-based meat.

Embodiment 4. The cell-based meat product of embodiments 1 to 3, wherein the cell-based meat product comprises no more than about 1 ug testosterone/kg dry mass of cell-based meat.

Embodiment 5. The cell-based meat product of any one of embodiments 1 to 4, wherein the cell-based meat product comprises no more than about 35 ng estradiol/kg dry mass of cell-based meat.

Embodiment 6. The cell-based meat product of any one of embodiments 1 to 5, wherein the cell-based meat product comprises about 50 g to about 90 g by weight of amino acids per 100 g dry mass.

Embodiment 7. The cell-based meat product of any one of embodiments 1 to 6, wherein the cell-based meat product comprises one or more of the following amino acids in the indicated amounts (expressed as g of amino acid/100 g total amino acid): Tryptophan about 1 to about 2.2, Threonine about 4.6 and 6.5, Isoleucine about 3.8 to about 5, Leucine about 6.1 to about 8.9, Lysine about 5.7 to about 8.8, Methionine about 0.14 to about 3.0, Cysteine about 1.5 to about 1.8, Phenylalanine about 3.7 to about 4.8, Tyrosine about 3.0 to about 5.2, Valine about 4.8 to about 6.1, Arginine about 7.0 to about 8.0, Histidine about 2.5 to about 4, Alanine about 5.0 to about 6.3, Aspartic acid about 8.6 to about 10.4, Glutamic acid about 12.5 to about 14.6, Glycine about 4.6 to about 9.8, Proline about 4.6 to about 6.8, Serine about 4.4 to about 5.3, and/or Hydroxyproline about 0.0 to 4.0.

Embodiment 8. The cell-based meat product of any one of embodiments 1 to 7, wherein the cell-based meat product has a moisture content of about 65% to about 95%.

Embodiment 9. The cell-based meat product of embodiment 8, wherein the moisture content is measured after harvesting, but before formulation.

Embodiment 10. The cell-based meat product of embodiment 8, wherein the moisture content is measured after formulation and a dehydration process, but before the addition of ingredients.

Embodiment 11. The cell-based meat product of any one of embodiments 1 to 10, wherein the cell-based meat product is a cell-based avian meat product.

Embodiment 12. The cell-based meat product of embodiment 11, wherein the cell-based avian meat product is a chicken cell-based meat product.

Embodiment 13. The cell-based meat product of embodiment 11, wherein the cell-based avian meat product is a duck cell-based meat product.

Embodiment 14. The cell-based meat product of any one of embodiments 1 to 10, wherein the cell-based meat product is a cell-based bovine meat product.

Embodiment 15. The cell-based meat product of any one of embodiments 1 to 14, wherein the cell-based meat product is a cell pellet.

Embodiment 16. The cell-based meat product of any one of embodiments 1 to 14, wherein the cell-based meat product is a cell sheet.

Embodiment 17. The cell-based meat product of any one of embodiments 1 to 16, wherein the cell-based meat product is generated from fibroblasts in culture.

Embodiment 18. The cell-based meat product of any one of embodiments 1 to 16, wherein the cell-based meat product is generated from myoblasts in culture.

Embodiment 19. The cell-based meat product of any one of embodiments 1 to 16, wherein the cell-based meat product is generated from a co-culture comprising fibroblasts and myoblasts in culture.

Embodiment 20. The cell-based meat product of any one of embodiments 16 to 19, wherein the culture further comprises adipocytes, endothelial cells, and/or cells of a mesodermal lineage.

Embodiment 21. The cell-based meat product of embodiment 19, wherein the ratio of fibroblasts to myoblasts in co-culture are at a ratio of about 95F:5M to about 5F:95M.

Embodiment 22. The cell-based meat product of any one of embodiments 1 to 21, wherein the cell-based meat product comprises at least about 0.5 mg Vitamin E/100 g wet mass of cell-based meat.

Embodiment 23. The cell-based meat product of any one of embodiments 1 to 22, wherein the cell-based meat product comprises one or more of the following fatty acids classes in the amounts indicated, expressed as % of that class over total fatty acids:
  a. saturated fatty acids content between about 29% to about 42%;
  b. monounsaturated fatty acids content between about 19% to about 54%; and
  c. polyunsaturated fatty acids content between about 5% to about 36%.

Embodiment 24. The cell-based meat product of any one of embodiments 1 to 23, wherein the cell-based meat product comprises a ratio of about 2:1 to 18:1 omega 6:3 fatty acids classes.

Embodiment 25. The cell-based meat product of embodiments 23 or 24, wherein the cell-based meat product is produced from chicken cells, duck cells, or bovine cells.

Embodiment 26. The cell-based meat product of embodiments 23 or 24, wherein the cell-based meat is generated in a medium in which the fatty acid content has been manipulated.

Embodiment 27. The cell-based meat product of any one of embodiments 1 to 25, wherein the cell-based meat product comprises at least one of the following textural features:
  a. cooked bite force from 450 g to about 2970 g; and
  b. cooked hardness from about 280 g to about 1900 g.

Embodiment 28. The cell-based meat product of any one of embodiments 1 to 27, the cell-based meat product has at least a 10× increase in stability and shelf life as compared to conventional meat.

Embodiment 29. The cell-based meat product of embodiment 28, wherein the increase in shelf life is measured at about 4° C.

Embodiment 30. The cell-based meat product of embodiment 28, wherein the increase in shelf life is measured at about 25° C.

Embodiment 31. A method of producing cell-based meat comprising:
  a. providing fibroblasts and/or myoblasts from a non-human organism;
  b. culturing the fibroblasts and/or myoblasts in media under suspension culture conditions, or adherent culture conditions, wherein the media is substantially free of serum and other components derived from an animal; and
  c. isolating the cells and producing the cell-based meat.

Embodiment 32. The method of embodiment 31, wherein the fibroblasts and/or myoblasts are provided at a ratio of about 95F:5M to about 5F:95M.

Embodiment 33. The method of any one of embodiments 31 to 32, wherein the cell-based meat product has at least a 2× increase in shelf life, as compared to conventional meat.

Embodiment 34. The method of any one of embodiments 31 to 33, wherein the method comprises adjusting the fatty acid content of the media, wherein the resulting cell-based meat product has a ratio of about 2:1 to about 18:1 of the omega 6:3 fatty acids classes.

Set 2

Embodiment 1. A slaughter-free meat product for dietary consumption exhibiting an extended shelf life, wherein the shelf life is extended compared to conventional meat obtained by slaughter, and wherein the shelf life is extended for at least 3 days following harvest.

Embodiment 2. The slaughter-free meat product of embodiment 1, wherein the extended shelf life is maintained for at least 3 days following harvest at about 0° C. to about 30° C.

Embodiment 3. The slaughter-free meat product of any one of embodiments 1 to 2, wherein the shelf life is determined after harvest, and prior to formulation.

Embodiment 4. The slaughter-free meat product of any one of embodiments 1 to 3, wherein the shelf life is determined after formulation.

Embodiment 5. The slaughter-free meat product of embodiment 3, wherein the shelf life is extended when the meat is harvested under non-aseptic conditions.

Embodiment 6. The slaughter-free meat product of any one of embodiments 1 to 5, wherein the shelf life is determined by measuring the total microbial count (TC), $E.$ $coli$/coliforms count (EC), $E.$ $coli$ microbial count, or the coliforms count.

Embodiment 7. The slaughter-free meat product of embodiment 6, wherein the TC measurement of conventional meat obtained by slaughter is at least 1.5× higher than that of the TC measurement of slaughter-free meat product.

Embodiment 8. The slaughter-free meat product of any one of embodiments 1 to 7, comprising no more than 1 cfus microbial contamination per g/wet mass.

Embodiment 9. The slaughter-free meat product of any one of embodiments 1 to 8, wherein the slaughter-free meat product comprises no more than about 1 ug steroid hormone.

Embodiment 10. The slaughter-free meat product of any one of embodiments 1 to 9, wherein the slaughter-free meat product comprises about 50 g to about 90 g by weight of amino acids per 100 g dry mass.

Embodiment 11. The slaughter-free meat product of any one of embodiments 1 to 10, wherein the slaughter-free meat product comprises one or more of the following amino acids in the indicated amounts (expressed as g of amino acid/100 g total amino acid): Tryptophan about 1 to about 2.2, Threonine about 4.6 and 6.5, Isoleucine about 3.8 to about 5, Leucine about 6.1 to about 8.9, Lysine about 5.7 to about 8.8, Methionine about 0.14 to about 3.0, Cysteine about 1.5 to about 1.8, Phenylalanine about 3.7 to about 4.8, Tyrosine about 3.0 to about 5.2, Valine about 4.8 to about 6.1, Arginine about 7.0 to about 8.0, Histidine about 2.5 to about 4, Alanine about 5.0 to about 6.3, Aspartic acid about 8.6 to about 10.4, Glutamic acid about 12.5 to about 14.6, Glycine about 4.6 to about 9.8, Proline about 4.6 to about 6.8, Serine about 4.4 to about 5.3, and/or Hydroxyproline about 0.0 to 4.0.

Embodiment 12. The slaughter-free meat product of any one of embodiments 1 to 11, wherein the slaughter-free meat product has a moisture content of about 65% to about 95%, wherein the moisture content is measured after harvest, but before formulation.

Embodiment 13. The slaughter-free meat product of any one of embodiments 1 to 12, wherein the slaughter-free meat product comprises at least about 0.5 mg Vitamin E/100 g wet mass of the slaughter-free meat product.

Embodiment 14. The slaughter-free meat product of any one of embodiments 1 to 13, wherein the slaughter-free meat product comprises one or more of the following fatty acids classes in the amounts indicated, expressed as % of that class over total fatty acids:
  a. saturated fatty acids content between about 10% to about 60%;
  b. monounsaturated fatty acids content between about 10% to about 60%; and
  c. polyunsaturated fatty acids content between about 1% to about 50%.

Embodiment 15. The slaughter-free meat product of any one of embodiments 1 to 14, wherein the slaughter-free meat product comprises a ratio of about 2:1 to 18:1 omega 6:3 fatty acids classes.

Embodiment 16. The slaughter-free meat product of any one of embodiments 1 to 15, wherein the slaughter-free meat product comprises slaughter-free chicken, duck, or bovine meat, and the conventional meat comprises chicken, duck or bovine meat obtained by slaughter.

Embodiment 17. The slaughter-free meat product of any one of embodiments 1 to 16, wherein the slaughter-free meat product is substantially free of vasculature.

Embodiment 18. The slaughter-free meat product of any one of embodiments 1 to 17, wherein the conventional meat is not processed.

Embodiment 19. A slaughter-free meat product for dietary consumption exhibiting a lower microbial contamination count as compared to conventional meat obtained by slaughter, wherein the lower microbial contamination count is exhibited for at least 3 days following harvest.

Embodiment 20. The slaughter-free meat product of embodiment 19, wherein the lower microbial contamination count is maintained for at least 3 days following harvest at about 0° C. to about 30° C.

Embodiment 21. The slaughter-free meat product of any one of embodiments 19 to 20, wherein the microbial contamination count is determined following harvest, and prior to formulation.

Embodiment 22. The slaughter-free meat product of any one of embodiments 19 to 21, wherein the slaughter-free meat product is maintained under non-aseptic conditions.

Embodiment 23. The slaughter-free meat product of any one of embodiments 19 to 22, wherein the microbial contamination count is determined by measuring the total microbial count (TC), $E.$ $coli$/coliforms count (EC), $E.$ $coli$ microbial count, or the coliforms count.

Embodiment 24. The slaughter-free meat product of any one of embodiments 19 to 23, comprising no more than 1 cfus microbial contamination per g/wet mass.

Embodiment 25. The slaughter-free meat product of any one of embodiments 19 to 24, wherein the TC measurement of conventional meat obtained by slaughter is at least 1.5× higher than that of the TC measurement of slaughter-free meat product.

Embodiment 26. The slaughter-free meat product of any one of embodiments 19 to 25, wherein the slaughter-free meat product comprises no more than about 1 ug steroid hormone.

Embodiment 27. The slaughter-free meat product of any one of embodiments 19 to 26, wherein the slaughter-free meat product comprises one or more of the following amino acids in the indicated amounts (expressed as g of amino acid/100 g total amino acid): Tryptophan about 1 to about 2.2, Threonine about 4.6 and 6.5, Isoleucine about 3.8 to about 5, Leucine about 6.1 to about 8.9, Lysine about 5.7 to about 8.8, Methionine about 0.14 to about 3.0, Cysteine about 1.5 to about 1.8, Phenylalanine about 3.7 to about 4.8, Tyrosine about 3.0 to about 5.2, Valine about 4.8 to about 6.1, Arginine about 7.0 to about 8.0, Histidine about 2.5 to about 4, Alanine about 5.0 to about 6.3, Aspartic acid about 8.6 to about 10.4, Glutamic acid about 12.5 to about 14.6, Glycine about 4.6 to about 9.8, Proline about 4.6 to about 6.8, Serine about 4.4 to about 5.3, and/or Hydroxyproline about 0.0 to 4.0.

Embodiment 28. The slaughter-free meat product of any one of embodiments 19 to 27, wherein the slaughter-free meat product comprises one or more of the following fatty acids classes in the amounts indicated, expressed as % of that class over total fatty acids:
  a. saturated fatty acids content between about 10% to about 50%;
  b. monounsaturated fatty acids content between about 10% to about 54%; and
  c. polyunsaturated fatty acids content between about 1% to about 50%.

Embodiment 29. The slaughter-free meat product of embodiments 19 to 28, wherein the slaughter-free meat product comprises a ratio of about 2:1 to 18:1 omega 6:3 fatty acids classes.

Embodiment 30. The slaughter-free meat product of embodiments 19 to 29, wherein the slaughter-free meat product comprises slaughter-free chicken, duck, or bovine meat, and the conventional meat comprises chicken, duck or bovine meat obtained by slaughter.

Embodiment 31. A method of producing a slaughter-free meat product exhibiting an increase in shelf life compared to unprocessed conventional meat obtained by slaughter, the method comprising:
  a. providing cells from a non-human organism;
  b. culturing the cells in media under suspension culture conditions or adherent culture conditions, wherein the media is substantially free of serum and other components derived from an animal; and
  c. isolating the cells and producing the slaughter-free meat product.

Embodiment 32. The method of embodiment 31, wherein the cells comprise myoblasts, fibroblasts, adipocytes, endothelial cells, cells of a mesoderm lineage, and combinations thereof.

Embodiment 33. The method of any one of embodiments 31-32, wherein the cells comprise at least fibroblasts and myoblasts, and the fibroblasts and myoblasts are provided at a ratio of about 95F:5M to about 5F:95M.

Embodiment 34. The method of any one of embodiments 31-33 the method comprises adjusting the fatty acid content of the media, wherein the resulting slaughter-free meat product has a ratio of about 2:1 to about 18:1 of the omega 6:3 fatty acids classes.

The inventions disclosed herein are further illustrated by the following additional examples that should not be construed as limiting. Those of skill in the art should, in light of the present disclosure, appreciate that many changes can be made to the specific embodiments which are disclosed and still obtain a like or similar result without departing from the spirit and scope of the invention.

All patent and non-patent documents referenced throughout this disclosure are incorporated by reference herein in their entirety.

EXAMPLES

Example 1: Generation of Cell Culture-Based Meat Products

By way of example, meat from *Gallus* (chicken), *Anas platyrhynchos* (duck), and *Bos taurus* (bovine, beef) was generated in culture as described below, and in Table 1.

Culture conditions: The cell sheets (tissues) and cells analyzed were generated by a monoculture or co-culture of fibroblasts (F) and myoblasts (M). All populations are polyclonal unless specified as monoclonal (e.g. Method 14).

Adherent culture format: Cells were thawed into vessels and grown in adherent culture to near confluence (70-90%). The cells were expanded 6 to 10-fold in adherent culture until reaching numbers appropriate to seed for tissue formation. Tissues were generated by seeding cells adherently at a target density (target range: 10,000-20,000 cells per cm2) and, if the tissue contained two or more cell types, at a specific ratio. The cells were cultured for an amount of time (10-20 days) in a media containing a specific amount of animal serum. The meat tissue was physically harvested at the end of culture and washed in a buffer to remove media components.

Suspension culture format: Cells were thawed into media containing specific amounts of animal serum and grown in suspension culture. Fresh media was added to maintain a density of 50,000 to 1,000,000 cells per mL to expand cell population.

Table 1 provides exemplary culture methods for the various meat products produced herein. All populations are polyclonal unless specified as monoclonal (e.g. Methods 14, 15, monoclonal myoblast population).

Key for the table—Fibroblast: F; Myoblast: M; Bovine serum: BS; Chicken serum: CS; Fetal bovine serum: FBS; Horse serum: HS; (High): media contained 8-10% of particular serum; (Low): media contained 1-2.5% of particular serum. DMIEM-F12 with 1000 FBS was used unless otherwise described in the seed train or tissue formation section

TABLE 1

Cell culture methods used to generate cell-based meat

| Method # | Sample ID | Culture Condition Cell Type(s) (ratio) | Culture format | Base media |
|---|---|---|---|---|
| 1 | *A. platyrhynchos* (duck) fibroblast/myoblast tissue 1 | Co-culture F/M (50/50) | Adherent | DMEM-F12 with FBS (High), BS (High), CS (Low), HS (Low) |
| 2 | *A. Platyrhynchos* (duck) fibroblast tissue 1 | Monoculture F | Adherent | DMEM-F12 with FBS (High), BS (High), CS (Low), HS (Low) |
| 3 | *Bos* (Cow) fibroblast tissue 1 | Monoculture F | Adherent | DMEM-F12 with FBS (High), BS (High), CS (Low), HS (Low) |
| 4 | *Gallus* (chicken) fibroblast tissue 1 | Monoculture F | Adherent | DMEM-F12 with FBS (High), CS (Low) |
| 5 | *Gallus* (chicken) fibroblast tissue 2 | Monoculture F | Adherent | DMEM-F12 with CS (High), BS (Low) |

TABLE 1-continued

Cell culture methods used to generate cell-based meat

| Method # | Sample ID | Culture Condition Cell Type(s) (ratio) | Culture format | Base media |
|---|---|---|---|---|
| 6 | *Gallus* (chicken) fibroblast tissue 3 | Monoculture F | Adherent | DMEM-F12 with CS (High), BS (High) |
| 7 | *Gallus* (chicken) fibroblast tissue 4 | Monoculture F | Adherent | DMEM-F12 with BS (High), CS (Low) |
| 8 | *Gallus* (chicken) fibroblast cells 1 | Monoculture F | Adherent | DMEM-F12 with 10% FBS |
| 9 | *Gallus* (chicken) fibroblast/myoblast tissue 1 | Co-culture F/M (30/70) | Adherent | DMEM-F12 with FBS (High), CS (Low) |
| 10 | *Gallus* (chicken) fibroblast tissue 5 | Monoculture F | Adherent | DMEM-F12 with BS (High), CS (Low) |
| 11 | *Gallus* (chicken) myoblast cells 1 | Monoculture M | Suspension | DMEM-F12 with BS (High), CS (Low) |
| 12 | *Gallus* (chicken) fibroblast/myoblast tissue 2 | Co-culture F/M (30/70) | Adherent | DMEM-F12 with BS (High), CS (Low |
| 13 | *Gallus* (chicken) fibroblast/myoblast tissue 3 | Co-culture F/M (50/50) | Adherent | DMEM-F12 with BS (High), CS (Low) |
| 14 | *Gallus* (chicken) fibroblast/myoblast tissue 4 | Co-culture F/Monoclonal M (50/50) | Adherent | DMEM-F12 with BS (High), CS (Low |
| 15 | *Gallus* (chicken) fibroblast/myoblast tissue 5 | Co-culture F/Monoclonal M (70/30) | Adherent | Chemically-defined media with BS (low) |
| 16 | *Gallus* (chicken) myoblast cells 2 | Monoculture M | Suspension | Chemically defined media formula. No serum |
| 17 | *Gallus* (chicken) myoblast cells 3 | Monoculture M | Suspension | SMEM-F12 with BS (high), CS (low) |

Example 2: Amino Acid Profiles of Cell Culture-Based Meat Products

Meat tissues were generated in culture, as described in Example 1 using Methods described and Table 1.

The amino acid profile of the cell-culture based meat products was assayed as follows. Total amino acid profiles include the summation of free and bound amino acids, whereas free amino acid profiles include amino acids that are not protein bound.

Sample preparation: About 100 mg of wet sample was obtained in a 1.7 mL microtube. The sample was freeze dried in the tube for 48 hours until completely dried.

Total Hydrolysis: About 4 mg of lyophilized tissue was placed into a hydrolysis tube (noting the actual mass of the sample). The samples were soaked in 500 μL of formic acid overnight, and then dried. Liquid phase hydrolysis on samples was performed (200 μL 6N hydrochloric acid/1% phenol @ 110° C. for 24 hrs), and then samples were dried. Samples were then vortexed, spun down and 50 μL was used for analysis. Thus, total hydrolysis was accomplished via hydrochloric acid digestion.

Free Hydrolysis: About 18 mg of lyophilized tissue was placed into a hydrolysis tube (noting the actual mass of the sample). The samples were dissolved in 1 mL 0.1N hydrochloric acid, and then sonicated for 15 min with glass beads (BioEruptor). The entire sample was then precipitated with 250 uL 10% 5-sulfosalicylic acid, and then allowed to stand for 15 minutes at room temperature, following which the samples were frozen at −20 C overnight. The samples were then centrifuged, and the supernatant was taken and AE-cys (or NorLeu) dilutions were prepared to final dilution as indicated. Samples were then vortexed, spun down and 50 μL was used for analysis. This method was employed for all amino acids except MET, CYS, and TRP, which require different hydrolysis conditions as hydrochloric acid destroys them. For MET and CYS, a separate hydrolysis was employed using performic acid, and TRP requires a basic hydrolysis employing sodium hydroxide was used.

Analysis: Acid-stable amino acids were assayed via Hitachi L-8900 and L-8800a analyzers that utilize a lithium citrate buffer system, which is optimized for physiological samples. The analyzers used ion-exchange chromatography to separate amino acids followed by a "post-column" ninhydrin reaction detection system. Each amino acid was identified by peak retention time (RT) and quantified by the peak area; representative RT values are listed below in Table 2 for the amino acids of interest.

TABLE 2

Peak Retention Times for Amino Acids

| Amino acid | Abbreviation | RT (min) |
|---|---|---|
| Aspartic acid | ASX | 8.5 |
| Threonine | THR | 12.2 |
| Serine | SER | 13.4 |
| Glutamic acid | GLX | 16.8 |
| Proline | PRO | 25.7 |
| Glycine | GLY | 26.9 |
| Alanine | ALA | 28.4 |
| Valine | VAL | 33.9 |
| Isoleucine | ILE | 53.4 |
| Leucine | LEU | 57.5 |
| Tyrosine | TYR | 61.4 |
| Phenylalanine | PHE | 66.4 |
| Lysine | LYS | 100.5 |
| Histidine | HIS | 103.2 |
| Arginine | ARG | 116 |

Tables 3-5 below summarize the amino acid (AA) profile data for several of the samples listed in Table 1—in some cases measurements were taken in duplicate or triplicate. Values are expressed as g/100 g of total amino acids. The column marked "Total" represents the total grams of amino acids, excluding TRP, CYS, MET, HYP, HYL, and was used to normalize the presented amino acid values. TRP, CYS, MET, HYP, and HYL were excluded as the measurements were inconsistent across all samples. NT=Not tested.

TABLE 3

Amino Acid Profiles

| Method ID | Total* | Tryptophan TRP | Threonine THR | Isoleucine ILE | Leucine LEU | Lysine LYS | Methionine MET |
|---|---|---|---|---|---|---|---|
| 1 | 96.13 | NT | 5.76 | 4.57 | 7.55 | 6.6 | NT |
| 1 | 96.50 | NT | 5.83 | 4.7 | 7.63 | 6.69 | NT |
| 1 | 96.25 | NT | 5.85 | 4.69 | 7.66 | 6.66 | NT |
| 3 | 96.00 | NT | 5.82 | 4.71 | 7.67 | 6.73 | NT |
| 3 | 96.19 | NT | 5.93 | 4.71 | 7.64 | 6.56 | NT |
| 4 | 96.70 | NT | 5.72 | 4.74 | 7.94 | 7.06 | NT |
| 4 | 97.44 | NT | 5.42 | 4.94 | 8.6 | 8.37 | NT |
| 5 | 91.50 | 2.22 | 5.3 | 4.35 | 7.55 | 6.94 | 2.95 |
| 6 | 92.12 | 2.12 | 5.22 | 4.39 | 7.71 | 7.17 | 2.95 |
| 7 | 92.26 | 1.98 | 5.32 | 4.37 | 7.63 | 7.21 | 2.96 |
| 7 | 99.98 | NT | 6.47 | 4.95 | 8 | 7.02 | NT |
| 8 | 95.15 | NT | 5.1 | 4.65 | 8.93 | 8.6 | 2.55 |
| 9 | 95.00 | NT | 5.09 | 4.74 | 8.61 | 8.8 | 2.7 |
| 9 | 93.47 | NT | 4.89 | 4.25 | 7.68 | 7.23 | 2.28 |
| 9 | 93.27 | NT | 4.97 | 4.25 | 7.56 | 7.06 | 2.24 |
| 10 | 97.24 | NT | 5.72 | 4.78 | 8.43 | 7.96 | 0.14 |
| 11 | 94.30 | NT | 5.65 | 4.68 | 8.05 | 7.57 | 2.46 |
| 11 | 93.72 | NT | 5.41 | 4.32 | 7.54 | 6.87 | 2.2 |

TABLE 4

Amino Acid Profiles

| Method ID | Cysteine CYS | Phenyl-alanine PHE | Tyrosine TYR | Valine VAL | Arginine ARG | Histidine HIS | Alanine ALA |
|---|---|---|---|---|---|---|---|
| 1 | NT | 4.14 | 4.09 | 5.78 | 7.63 | 3.46 | 5.3 |
| 1 | NT | 4.18 | 4.13 | 5.86 | 7.52 | 3.47 | 5.25 |
| 1 | NT | 4.15 | 4.08 | 5.83 | 7.54 | 3.37 | 5.27 |
| 3 | NT | 4.2 | 4.04 | 5.81 | 7.47 | 3.36 | 5.29 |
| 3 | NT | 4.17 | 4.17 | 5.86 | 7.57 | 3.37 | 5.2 |
| 4 | NT | 4.29 | 4.05 | 5.92 | 7.59 | 3.56 | 5.42 |
| 4 | NT | 4.62 | 3.96 | 5.86 | 7.45 | 3.94 | 5.52 |
| 5 | 1.72 | 4.27 | 3.93 | 5.33 | 7.07 | 3.51 | 5.02 |
| 6 | 1.6 | 4.38 | 3.92 | 5.35 | 7.17 | 3.52 | 5.08 |
| 7 | 1.54 | 4.09 | 3.77 | 5.5 | 7.21 | 3.45 | 5.12 |
| 7 | NT | 4.23 | 5.15 | 5.88 | 7.95 | 2.51 | 5.54 |
| 8 | 1.8 | 4.76 | 3.94 | 6.1 | 7.6 | 3.85 | 5.63 |
| 9 | 1.7 | 4.65 | 3.89 | 5.95 | 7.37 | 3.9 | 5.58 |
| 9 | 1.72 | 4.39 | 3.69 | 5.32 | 7.13 | 3.38 | 5.95 |
| 9 | 1.69 | 4.42 | 3.72 | 5.37 | 7.12 | 3.46 | 5.91 |
| 10 | 1.7 | 4.52 | 3.98 | 6.07 | 7.56 | 3.79 | 5.6 |
| 11 | 1.82 | 4.34 | 4.01 | 5.89 | 7.33 | 3.83 | 5.37 |
| 11 | 1.67 | 4.13 | 3.73 | 5.53 | 7.41 | 3.41 | 5.71 |

TABLE 5

Amino Acid Profiles

| Method ID | Alanine ALA | Aspartic acid ASX | Glutamic acid GLX | Glycine GLY | Proline PRO | Serine SER | Hydroxy-proline HYP |
|---|---|---|---|---|---|---|---|
| 1 | 5.3 | 9.91 | 13.52 | 7.03 | 5.99 | 4.8 | 1.58 |
| 1 | 5.25 | 9.98 | 13.57 | 6.8 | 6.04 | 4.85 | 1.32 |
| 1 | 5.27 | 9.87 | 13.51 | 6.89 | 6.07 | 4.81 | 1.26 |
| 3 | 5.29 | 9.82 | 13.47 | 6.73 | 6.09 | 4.79 | 1.37 |
| 3 | 5.2 | 9.91 | 13.49 | 6.82 | 5.95 | 4.84 | 1.28 |
| 4 | 5.42 | 9.71 | 13.73 | 6.39 | 5.75 | 4.83 | 1.07 |
| 4 | 5.52 | 9.97 | 13.92 | 5 | 4.91 | 4.96 | NT |
| 5 | 5.02 | 9.19 | 13.55 | 5.63 | 5.16 | 4.7 | 1.02 |
| 6 | 5.08 | 9.31 | 13.64 | 5.39 | 5.16 | 4.71 | 0.64 |
| 7 | 5.12 | 9.41 | 13.8 | 5.56 | 5.03 | 4.79 | 0.86 |
| 7 | 5.54 | 10.39 | 14.64 | 6.18 | 5.78 | 5.29 | 0 |
| 8 | 5.63 | 9.48 | 12.63 | 4.56 | 4.59 | 4.73 | 0 |
| 9 | 5.58 | 9.57 | 12.47 | 4.94 | 4.78 | 4.66 | 0 |
| 9 | 5.95 | 9.15 | 13.29 | 7.06 | 5.49 | 4.57 | 1.51 |
| 9 | 5.91 | 9.05 | 13.15 | 7.12 | 5.6 | 4.51 | 1.71 |
| 10 | 5.6 | 9.89 | 13.24 | 5.33 | 5.3 | 5.07 | 0.36 |
| 11 | 5.37 | 9.57 | 12.67 | 5.44 | 5.05 | 4.85 | 0.8 |
| 11 | 5.71 | 9.38 | 12.65 | 6.95 | 6.01 | 4.67 | 1.64 |

Tables 6-8 show the composite average amino acid values (represented as 0 total amino acids) for chicken, duck, and bovine separately. The 00 of total amino acids are represented as the g/100 g value for each individual amino acid normalized by the summation across all measured analytes, excluding tryptophan (TRP), cysteine (CYS), methionine (MET), hydroxyproline (HYP), and hydroxylysine (HYL) as those parameters were not measured consistently across all samples. Thus, the 00 of total values allow for direct comparison of all samples, regardless of whether TRP, CYS, MET, HYP, and HYL were specifically measured.

Table 9 shows the data of Tables 6-8 combined—all cell-based meat samples (composite of methods in Table 1) amino acid composition data.

TABLE 6

Chicken cell-based meat amino acid composition

Table 6: Chicken - % Total AA

|  | THR | ILE | LEU | LYS | MET | CYS |
|---|---|---|---|---|---|---|
| AVG | 5.53 | 4.60 | 7.91 | 7.28 | 2.34 | 1.70 |
| STDEV | 0.40 | 0.22 | 0.44 | 0.70 | 0.83 | 0.08 |
| N | 18 | 18 | 18 | 18 | 10 | 10 |
| 95% CI | 0.19 | 0.10 | 0.20 | 0.32 | 0.51 | 0.05 |
| MIN | 4.89 | 4.25 | 7.54 | 6.56 | 0.14 | 1.54 |
| MAX | 6.47 | 4.95 | 8.93 | 8.80 | 2.96 | 1.82 |

|  | PHE | TYR | VAL | ARG | HIS | ALA |
|---|---|---|---|---|---|---|
| AVG | 4.33 | 4.01 | 5.73 | 7.43 | 3.51 | 5.43 |
| STDEV | 0.20 | 0.32 | 0.26 | 0.23 | 0.32 | 0.27 |
| N | 18 | 18 | 18 | 18 | 18 | 18 |
| 95% CI | 0.09 | 0.15 | 0.12 | 0.10 | 0.15 | 0.12 |

TABLE 6-continued

Chicken cell-based meat amino acid composition

Table 6: Chicken - % Total AA

|     | THR | ILE | LEU | LYS | MET | CYS |
|---|---|---|---|---|---|---|
| MIN | 4.09 | 3.69 | 5.32 | 7.07 | 2.51 | 5.02 |
| MAX | 4.76 | 5.15 | 6.10 | 7.95 | 3.94 | 5.95 |

|     | ASX | GLX | GLY | PRO | SER | HYP |
|---|---|---|---|---|---|---|
| AVG | 9.64 | 13.39 | 6.10 | 5.49 | 4.80 | 0.97 |
| STDEV | 0.35 | 0.54 | 0.86 | 0.50 | 0.18 | 0.59 |
| N | 18 | 18 | 18 | 18 | 18 | 17 |
| 95% CI | 0.16 | 0.25 | 0.40 | 0.23 | 0.08 | 0.28 |
| MIN | 9.05 | 12.47 | 4.56 | 4.59 | 4.51 | 0.00 |
| MAX | 10.39 | 14.64 | 7.12 | 6.09 | 5.29 | 1.71 |

TABLE 7

Duck cell-based meat amino acid composition

Table 7: Duck - % Total AA

|     | THR | ILE | LEU | LYS | MET | CYS |
|---|---|---|---|---|---|---|
| AVG | 5.10 | 3.99 | 6.42 | 6.35 | 2.09 | 1.61 |
| STDEV | 0.09 | 0.15 | 0.43 | 0.33 | 0.06 | 0.09 |
| N | 3 | 3 | 3 | 3 | 3 | 3 |
| 95% CI | 0.10 | 0.17 | 0.48 | 0.38 | 0.07 | 0.10 |
| MIN | 5.01 | 3.82 | 6.10 | 6.09 | 2.02 | 1.51 |
| MAX | 5.18 | 4.12 | 6.90 | 6.73 | 2.13 | 1.68 |

|     | PHE | TYR | VAL | ARG | HIS | ALA |
|---|---|---|---|---|---|---|
| AVG | 4.08 | 3.26 | 4.99 | 7.36 | 2.76 | 6.15 |
| STDEV | 0.19 | 0.18 | 0.23 | 0.25 | 0.15 | 0.17 |
| N | 3 | 3 | 3 | 3 | 3 | 3 |
| 95% CI | 0.21 | 0.21 | 0.26 | 0.28 | 0.17 | 0.19 |
| MIN | 3.87 | 3.05 | 4.78 | 7.12 | 2.65 | 5.96 |
| MAX | 4.23 | 3.40 | 5.24 | 7.62 | 2.93 | 6.28 |

|     | ASX | GLX | GLY | PRO | SER | HYP |
|---|---|---|---|---|---|---|
| AVG | 8.78 | 13.16 | 8.76 | 6.56 | 4.56 | 3.48 |
| STDEV | 0.24 | 0.31 | 0.73 | 0.34 | 0.08 | 0.54 |
| N | 3 | 3 | 3 | 3 | 3 | 3 |
| 95% CI | 0.28 | 0.35 | 0.83 | 0.39 | 0.09 | 0.61 |
| MIN | 8.61 | 12.80 | 7.95 | 6.17 | 4.49 | 3.01 |
| MAX | 9.06 | 13.36 | 9.38 | 6.79 | 4.65 | 4.07 |

TABLE 8

Beef cell-based meat amino acid composition

Table 8: Beef - % Total AA

|     | THR | ILE | LEU | LYS | MET | CYS |
|---|---|---|---|---|---|---|
| AVG | 4.60 | 3.96 | 7.03 | 5.96 | 2.01 | 1.53 |
| STDEV | 0.02 | 0.09 | 0.24 | 0.39 | 0.01 | 0.06 |
| N | 2 | 2 | 2 | 2 | 2 | 2 |
| 95% CI | 0.03 | 0.13 | 0.33 | 0.54 | 0.01 | 0.09 |
| MIN | 4.58 | 3.89 | 6.86 | 5.68 | 2.00 | 1.48 |
| MAX | 4.61 | 4.02 | 7.20 | 6.23 | 2.01 | 1.57 |

|     | PHE | TYR | VAL | ARG | HIS | ALA |
|---|---|---|---|---|---|---|
| AVG | 3.82 | 3.37 | 4.89 | 7.25 | 2.74 | 6.07 |
| STDEV | 0.14 | 0.02 | 0.13 | 0.28 | 0.07 | 0.10 |
| N | 2 | 2 | 2 | 2 | 2 | 2 |
| 95% CI | 0.20 | 0.03 | 0.18 | 0.39 | 0.10 | 0.14 |
| MIN | 3.72 | 3.35 | 4.80 | 7.05 | 2.69 | 6.00 |
| MAX | 3.92 | 3.38 | 4.98 | 7.45 | 2.79 | 6.14 |

TABLE 8-continued

Beef cell-based meat amino acid composition

Table 8: Beef - % Total AA

|     | ASX | GLX | GLY | PRO | SER | HYP |
|---|---|---|---|---|---|---|
| AVG | 8.77 | 13.03 | 9.27 | 6.26 | 4.50 | 3.21 |
| STDEV | 0.22 | 0.46 | 0.79 | 0.40 | 0.06 | 0.42 |
| N | 2 | 2 | 2 | 2 | 2 | 2 |
| 95% CI | 0.30 | 0.64 | 1.10 | 0.56 | 0.08 | 0.58 |
| MIN | 8.61 | 12.70 | 8.71 | 5.97 | 4.46 | 2.91 |
| MAX | 8.92 | 13.35 | 9.83 | 6.54 | 4.54 | 3.50 |

TABLE 9

All cell-based meat samples (composite of methods in Table 1) amino acid composition (g amino acid per 100 g sample)

|     |     | AVG | STDEV | N | MIN | MAX |
|---|---|---|---|---|---|---|
| Tryptophan | TRP | 1.67 | 0.60 | 5 | 1 | 2.22 |
| Threonine | THR | 5.39 | 0.46 | 23 | 4.58 | 6.47 |
| Isoleucine | ILE | 4.46 | 0.33 | 23 | 3.82 | 4.95 |
| Leucine | LEU | 7.64 | 0.68 | 23 | 6.1 | 8.93 |
| Lysine | LYS | 7.05 | 0.78 | 23 | 5.68 | 8.80 |
| Methionine | MET | 2.25 | 0.68 | 15 | 0.14 | 2.96 |
| Cysteine | CYS | 1.66 | 0.10 | 15 | 1.48 | 1.82 |
| Phenylalanine | PHE | 4.25 | 0.25 | 23 | 3.72 | 4.76 |
| Tyrosine | TYR | 3.86 | 0.41 | 23 | 3.05 | 5.15 |
| Valine | VAL | 5.56 | 0.41 | 23 | 4.78 | 6.10 |
| Arginine | ARG | 7.40 | 0.23 | 23 | 7.05 | 7.95 |
| Histidine | HIS | 3.34 | 0.43 | 23 | 2.51 | 3.94 |
| Alanine | ALA | 5.58 | 0.38 | 23 | 5.02 | 6.28 |
| Aspartic acid | ASX | 9.45 | 0.49 | 23 | 8.61 | 10.39 |
| Glutamic acid | GLX | 13.32 | 0.50 | 23 | 12.47 | 14.64 |
| Glycine | GLY | 6.72 | 1.46 | 23 | 4.56 | 9.83 |
| Proline | PRO | 5.69 | 0.61 | 23 | 4.59 | 6.79 |
| Serine | SER | 4.74 | 0.20 | 23 | 4.46 | 5.29 |

Collectively, the amino acid profiles of the meat are comparable to conventional meat (FIG. 1), however there are critical differences. For example, hydroxyproline concentrations in the cell-based meat is higher than in conventional meat (USDA database Food Central Database [https://fdc.nal.usda.gov/]). Comparison to cell-based meat is shown in Table 10 (units shown in grams of hydroxyproline per 100 g of total protein). Concentrations are shown for conventional and cell-based meat beef, duck and chicken. The cell-based meat was generated using Methods 2, 3 and 7 from Table 1. Hydroxyproline concentrations were elevated in the cell-based meat in three species used as comparators.

TABLE 10

Hydroxyproline Concentrations (g of Hydroxyproline/100 g total protein)

| | USDA/Literature | | | Experimental Analysis | | | |
|---|---|---|---|---|---|---|---|
| | Conventional | | | | Cell-based meat | | |
| | Beef | Duck | Chicken | Chicken | Beef | Duck | Chicken |
| Mean | 0.839 | 0.852 | 0.371 | 0.223 | 3.205 | 3.477 | 1.424 |
| SD | 0.489 | 0.167 | 0.160 | 0.146 | 0.417 | 1.521 | 0.288 |
| N | 8 | 40 | 8 | 4 | 2 | 3 | 10 |

Figure 2:
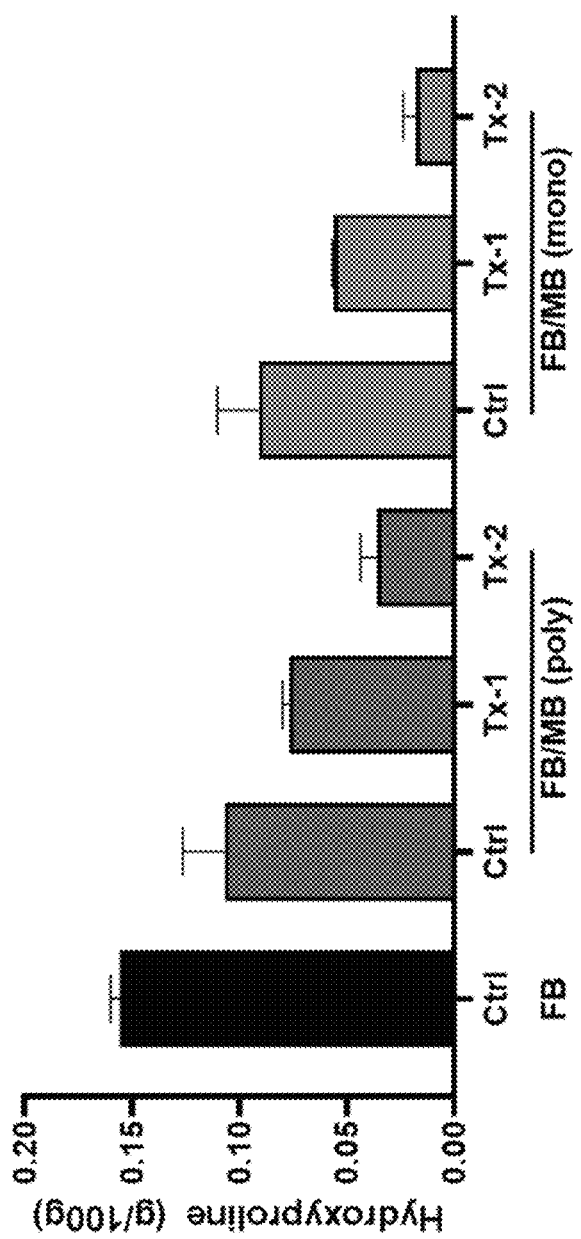
FIG. 2 shows the mean concentration range of hydroxyproline in exemplary cell-based meat samples (expressed as grams of hydroxyproline per 100 g of wet mass of cell-based meat).

FIG. 2 and Table 11 show the hydroxyproline concentrations for chicken cell-based meat for cell-based meat generated from Methods 7, 13, and 14, with further treatments. FIG. 2 shows the hydroxyproline concentrations in grams per 100 g of wet mass of cell-based meat. Hydroxyproline mean concentration across the cell-based meat ranges between 0.15 and 0.17 g/100 g wet mass of cell-based meat (FIG. 2). Table 11 shows the hydroxyproline concentrations in grams per 100 g total protein. The control conditions (Ctrl) were generated using Methods 7, 13, 14 from Table 1 for FB, FB/MB (poly), and FB/MB (mono), respectively. Hydroxyproline levels are elevated in cell-based meat generated from fibroblast cultures alone, as compared to the conventional counterpart. When myoblasts (MB) are added to the culture system either as a polyclonal cell mixture (mixed population of myoblasts) (e.g. Method 13 from Table 1) or monoclonal myoblast cell mixture (Method 14 from Table 1) (single-cell isolated from a mixed population and expanded), the hydroxyproline concentration is reduced to close to that of conventional meat. Hydroxyproline concentrations further decrease using modified culture conditions (Treatment 1 Ursoloic acid, 20 mM; or Treatment 2 Leucine, 20 mM). These treatments were applied to Methods 13 and 14 from Table 1.

TABLE 11

Hydroxyproline Concentrations (g/100 g total protein)

| | FB | FB/MB(poly) | | | FB/MB(mono) | | |
|---|---|---|---|---|---|---|---|
| | Cnt | Cnt | Tx-1 | Tx-2 | Cnt | Tx-1 | Tx-2 |
| Mean | 1.424 | 0.898 | 0.649 | 0.308 | 0.814 | 0.510 | 0.162 |
| SD | 0.288 | 0.449 | 0.044 | 0.112 | 0.438 | 0.014 | 0.090 |
| N | 10 | 8 | 3 | 3 | 6 | 3 | 3 |

Example 3: Assay for Microbial Contamination of the Cell-Based Meat Product

The cell-based meat tissues were assessed for microbial contamination, for example for coliform bacteria, yeast, mold, *Salmonella* and *Listeria*.

These studies were performed by a third-party lab, Anresco Laboratories. Standard plate counts (SPC), *E. coli*/coliforms, and yeast/mold were determined by standard FDA Biological Analytical Method protocols. AOAC methods were used for *Salmonella* (AOAC 2011.03), *Listeria* (AOAC 2004.06), and *Staphylococcus* (AOAC 2003.07).

Briefly, SPC were accomplished by preparing decimal dilutions of a cell-based meat homogenate and pipetting 1 mL aliquots per dilution into separate, duplicate, approximately marked petri dishes, to which 12-15 mL of plate count agar was added. Sample dilutions and agar medium were mixed thoroughly and the agar allowed to solidify. The solidified petri dishes were inverted and incubated at 35° C. for 48±2 hours, after which time plate counts were read. (https://www.fda.gov/food/laboratory-methods-food/bam-aerobic-plate-count#conventional)

*E. coli*/coliform measurements were determined by preparing 50 g of cell-based meat homogenized sample to 450 mL of Butterfield's phosphate buffer and mixed; decimal dilutions were prepared and 1 mL volume aliquoted into each of 3 lauryl tryptose (LST) broth for a 3 tube most probable number (MPN). LST tubes were incubated at 35° C. and examined after 24±2 hours to observe for gas displacement or effervescence; any gas-negative tubes were incubated for an additional 24 hours to confirm a negative. From each gassing LST tube, to confirm coliforms, a loopful of sample was transferred to a tube of brilliant green lactose bile (BGLB) broth and incubated at 35° C. for 48+3 hours. MPN was calculated based on the proportion of confirmed gassing LST tubes for 3 consecutive dilutions. From each gassing LST tube, to confirm for *E. coli*, a loopful of sample was transferred to a tube of EC broth and incubated at 44.5° C. for 24±2 hours. Any negative results were re-incubated and examined again at 48 hours. Further, each gassing EC tube was sampled by removing a loopful of broth and streak-isolating on a L-EMB agar plate at 35° C. for 18-24 hours; any *E. coli* colonies were transferred to PCA slants and further incubated at 35° C. for 18-24 hours. MPN was calculated based on the proportion of EC tubes in 3 successive dilutions that contain *E. coli*. (https://www.fda.gov/food/laboratory-methods-food/bam-4-enumeration-escherichia-coli-and-coliform-bacteria#conventional)

Yeast/mold counts were obtained by analyzing 25-50 g cell-based meat sample digested in 0.1% peptone water to achieve a 10' dilution and homogenized in a stomacher for 2 min or blending for 30-60 s. Spread-plate or pour-plate plating was performed, and incubated in the dark at 25° C. Plates were counted after 5 days; negative plates were incubated for an additional 48 hours. (https://www.fda.gov/food/laboratory-methods-food/bam-yeasts-molds-and-mycotoxins)

Table 12 provides a comparison of contaminants in the cell-based meat versus conventional grocery store meat. Conventional duck meat, and especially conventional beef had significantly higher amounts of microbial contamination.

The conventional duck meat was purchased at a local grocery store (Berkeley, Calif.). The meat was separated from skin and fat and was finely chopped with a sterilized knife and cutting board. Meat was packed into 50 mL falcon tubes & sealed. The closed tube was sprayed with 70% ethanol and frozen at −80° C. Samples were frozen at −80° C. for, then held at 4° C. prior to testing.

The cell-based duck meat was a combination of tissues using Methods 1 and 2 described in Table 1. Tissues were removed from frozen storage, mixed, and chopped using a sterilized cutting board and knife. Meat was packed into 50 mL falcon tubes & sealed. The closed tubes were sprayed with 70% ethanol and frozen at −80° C. Samples were frozen at −80° C. for, then held at 4° C. prior to testing.

Extra lean (97% lean) ground beef was purchased from a local grocery store (Berkeley, Calif.). Beef was packed into 50 mL falcon tubes directly. The tubes were sealed and sprayed with 70% ethanol. Tubes were frozen at −80° C. Samples were frozen at −80° C. for, then held at 4° C. prior to testing.

The cell-based beef meat was a combination of tissues from using Method 3 in Table 1. Tissues were removed from frozen storage, mixed, and chopped using a sterilized cutting board and knife. Meat was packed into 50 mL falcon tubes & sealed. The closed tubes were sprayed with 70% ethanol and frozen at −80° C. Samples were frozen at −80° C. for, then held at 4° C. prior to testing.

TABLE 12

Contaminant Comparison in Conventional and Cell-Based Meat

| Sample | Standard Plate Count (cfu/g) | Confirmed Coliforms (cfu/g) | E. coli (cfu/g) | Yeast (cfu/g) | Mold (cfu/g) | Salmonella (per 25 g) | Listeria (per 25 g) | CP Staph (cfu/g) |
|---|---|---|---|---|---|---|---|---|
| Conventional Duck | 100 | <10 | <10 | <10 | <10 | Negative | Negative | <10 |
| Cell-based Duck | <100 | <10 | <10 | <10 | <10 | Negative | Negative | <10 |
| Conventional Beef | 6000000 | 1300 | <10 | 2300 | <10 | Negative | Positive - L. monoctogenes detected | <10 |
| Cell-based Beef | <100 | <10 | <10 | <10 | <10 | Negative | Negative | <10 |

In further experiments, CompactDry plates were used to assess total aerobic counts and E. coli/coliform counts for cell-based meat samples and conventional meat samples; all evaluated samples were uncooked and raw.

A CompactDry protocol was deployed, which involved collecting a 1 g sample size with ethanol-sterilized supplies and transferring to a sterile tube; sterile Butterfield's phosphate buffer was added to maintain a ratio of 25 g sample to 225 mL of buffer. Tubes were vortexed, sat at room temperature for 10 min to transfer any bacteria to solution, then centrifuged at 300×g for 5 min to pull solids to the bottom; the supernatant was collected into a sterile tube and decimal dilutions prepared. 1 mL aliquots per dilution were plated onto the Total Count CompactDry™ TC and CompactDry™ EC plates for total aerobic counts (TC) and E. coli/coliforms (EC), respectively. Plates were incubated according to manufacturer specifications, and colonies counted as cfu/mL and converted to cfu/g based on the 25 g per 225 mL sample digestion ratio.

In general, the cell-based meat recoveries were low, usually less than the limit of detection (~10 cfu/g) for the assay and were thus not detected (ND), Table 13. More specifically, different batches of cell-based duck meat yielded from ND (<9 cfu/g) to 54 cfu/g for TC, and ND (<9 cfu/g) for total EC. For TC, cell-based beef samples yielded ND (<9 cfu/g) and cell-based chicken samples yielded from ND (<9 cfu/g) to 18 cfu/g. When cell-based duck and beef samples (with low total aerobic counts) were intentionally contaminated with conventional raw chicken (in Table 13 represented as cell-based sample "contaminated with chicken"), the TC spiked to >900 cfu/g, indicating utility of the assay with the sample matrix and confirming that no signal suppression was occurring due to matrix effects. Conventional raw beef and chicken samples both exhibited >900 cfu/g TC, and 315 cfu/g and >900 cfu/g EC, respectively. Compared to conventional raw meat samples, the cell-based meat samples all exhibited not detectable-to-low (<100 cfu/g) TC and EC counts indicating significantly less bioburden. FIG. 3 shows representative CompactDry plates indicating bacteria colonies, specifically showing EC and TC results for cell-based duck, conventional beef, and conventional chicken. This is quantified in Table 13.

TABLE 13

Bioburden of Conventional and Cell-Based Meat Samples

| Sample | Total aerobic counts, cfu/g | E. coli/coliforms, cfu/g |
|---|---|---|
| Conventional beef | >1000 | 350 |
| Conventional chicken | >1000 | >1000 |
| Cell-Based duck | 60 | <10 |
| Cell-Based duck, contaminated with chicken | >1000 | Not measured |
| Cell-Based beef | <10 | Not measured |
| Cell-Based beef, contaminated with chicken | >1000 | Not measured |
| Cell-Based chicken | <10 to 20 | Not measured |
| Cell-Based chicken, contaminated with chicken | >1000 | Not measured |

Example 4: Assay for Fatty Acid Content of Cell-Based Meat Product

The majority of data in this section involved assaying fatty acid profiles via a GC-FAME method (Method FA1), whereby samples underwent direct hydrolysis (using hydrochloric acid under heat with the sample dissolved in chloroform and ethanol) to break down the sample matrix, liberate the triglycerides (TG), and convert TG to fatty acids. Fatty acids were recovered via ether extraction and collected as the non-polar layer. Fatty acids were derivatized to their fatty acid methyl ester (FAME) counterparts via methanolic sulfuric acid, and the final FAME compounds recovered via ether extraction. The non-polar FAME-containing layer was injected for analysis via GC-FID. Individual FAME compounds were identified based on retention time, and quantified by area under the peak as compared to a standard curve. Recovery was evaluated based on a triglyceride internal standard. The data presented in FIG. 8 were assayed via a technically different (although similar) method (Method FA2), according to AOCS CE 1F-96, whereby gas chromatography was employed to separate fatty acid derivatives (FAME) by their chain length, degree of saturation/unsaturation, and position of unsaturation.

In both methods, the raw values recovered from the analysis are reported as each fatty acid's percentage of the total fatty acid. In Method FA1, the values reported from the assay were ug fatty acid per g of wet mass. The % of total fatty acids are represented as the g/100 g value for each individual fatty acid normalized by the summation across all measured fatty acid analytes. Method FA2 reported fatty acid as percent of total fat.

Table 14 shows the total fatty acid analysis for cell-based meat. Total FA was determined in the cell-based meat prepared, using the methods of Table 1, as indicated. The data in table is measured as % of wet mass. When the cell-based meat is adjusted to mimic the moisture content of conventional meat (on cell-based meat which had undergone a forced air dehydration process to adjust moisture content to between 65% to 85%), as is typically measured and recorded by the USDA, the % FA went up to a maximum of about 5%.

TABLE 14

Total Fatty Acid Analysis

| Method name (Table 1) | Percent Total FA (%) of wet mass |
|---|---|
| 7 | 0.97 |
| 14 | 0.88 |
| 14 | 0.77 |
| 17 | 1.11 |
| 17 | 2.17 |
| 13 | 1.12 |
| 13 | 1.15 |
| 14 | 1.45 |
| 14 | 1.25 |
| 14 | 0.96 |
| 17 | 0.57 |
| 17 | 1.15 |
| 17 | 1.01 |
| 17 | 0.86 |
| 16 | 0.96 |
| 14 | 1.01 |
| 14 | 1.2 |
| 16 | 0.68 |
| 16 | 0.64 |
| 16 | 0.66 |
| 7 | 1.12 |
| 7 | 1.07 |
| 7 | 1.4 |
| 14 | 1.38 |
| Avg | 1.06 |
| Min | 0.57 |
| Max | 2.17 |
| Store-bought chicken | 3.96 |
| Store-bought chicken | 3.98 |
| Store-bought chicken | 4.13 |
| Avg | 4.02 |

FIG. 4 shows total fatty acid composition for saturated, monounsaturated and polyunsaturated fatty acids across the samples (N=24) including representative samples using each method in Table 1. The data are presented as percent of FA class/total FA. All samples (Table 1, 1-15) were in serum-containing media except suspension monoculture M (Method 16, Table 1) which was in chemically-defined (CD) cell culture media. The figure shows distribution of fatty acids derived from all species cell-based meat prototypes across four major fatty acid class designations (saturated fatty acids, monounsaturated fatty acids, polyunsaturated fatty acids and highly unsaturated fatty acids (HIUFA)). The ends of the box are the upper and lower quartiles, so the box spans the interquartile range, the median is marked by a vertical line inside the box, the whiskers or lines that bracket the box are the two lines outside the box that extend to the highest and lowest observations.

Figure 5:
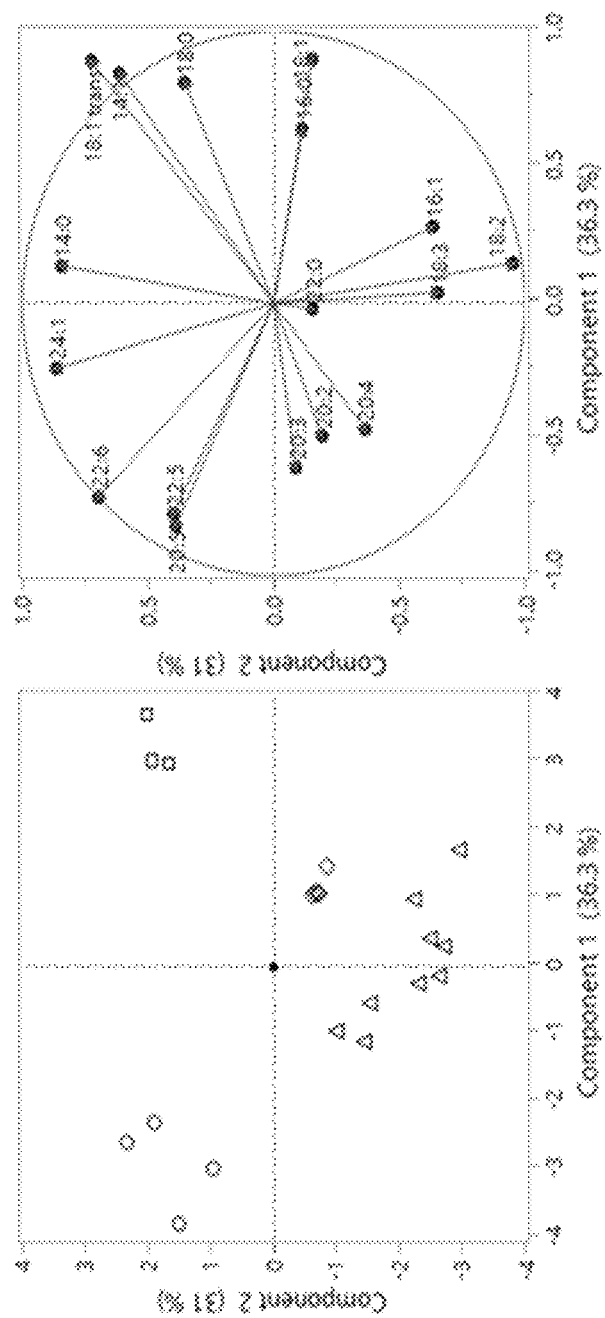
FIG. 5 shows the principal component analysis (PCA) of fatty acid data, gathered from the USDA database for conventional meat products.

FIG. 5 shows the PCA of USDA species FA. It shows that FA are different across species but similar in like species (e.g. poultry). Principal component analysis (PCA) of fatty acid data were gathered from the USDA database meat products, FIG. 5. The graph on the left shows the principal components of the analysis. Triangles represent poultry products, circles represent fish products, squares are beef, and diamonds are pork. This analysis accounts for 66.3% of the variation found in the fatty acid data. The graph on the right shows the directional and magnitude effects that each fatty acid has on the analysis of the components. From this analysis it is clear that the different types of meat (chicken, pork, beef, and fish) cluster around each other in separate and distinct groups based on the fatty acid profile of each meat. In conventional meat, diet significantly affects the fatty acids profile. Likewise, fatty acid profiles are distinct for different species.

Figure 6:
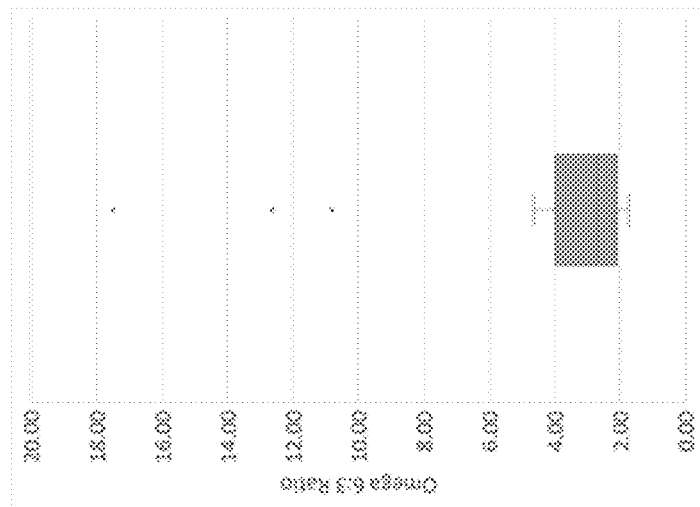
FIG. 6 shows the ratio of Omega 6 to 3 fatty acids in an exemplary sample of slaughter-free cell-based chicken meat.

FIG. 6 shows the ratio of Omega 6 to 3 fatty acids in cell-based chicken meat N=23. The outlier data points were all derived from chemically-defined (CD) cell culture media per Method 16 from Table 1. Conventional chicken (locally procured from grocery store) meat ratio of Omega 6:3 fatty acid were >18:1 in a sample size of n=3.

The methods provided herein can alter specific lipid profiles to achieve desired flavor characteristics or fatty acid profiles such as Omega 3/6 ratio through several mechanisms:
  a. The presence of serum in the media can affect fatty acid profiles. FIG. 7 shows the fatty acid percentages in serum free media vs. media containing serum.
  b. Serum of different sources imparts different fatty acid profiles in cultured tissues. (FIG. 8)
  c. Isolated clones from a polyclonal population affects FA profile as well. Myoblast Clone 7 vs 8 (FIG. 9).
  d. Fatty acids profiles are affected by media composition and by the addition of media components including compounds added to change FA composition like an agonist, or riboflavin (for example). Adjustments to media can impact fat profiles. (FIG. 10, FIG. 11).

FIG. 10. Tissues were formed using a co-culture method (described in the Method 15 in Table 1) using culture media with enhanced levels of various compounds to modulate specific biochemical pathways In FIG. 10, Agonist T0901317 was titrated into cell culture media. The global effect on fatty acid concentrations are shown. Agonist T0901317 targets the Liver X Receptor β (LXRβ). Inhibition of LXRβ, up-regulates stearoyl-CoA Desaturase (SCD) synthesis, resulting in the further conversion of saturated fatty acids to unsaturated fatty acid (e.g. steric acid-18:0 oleic acid-18:1 and linoleic acid-18:2.

FIG. 11 Tissue were formed using a co-culture method (described in Method 15 in Table 1) using culture media with enhanced levels of various compounds to modulate specific biochemical pathways. In the figure, Riboflavin, a vitamin and common co-factor, was titrated into cell culture media. The global effects on fatty acid concentrations are shown.

Figure 12:
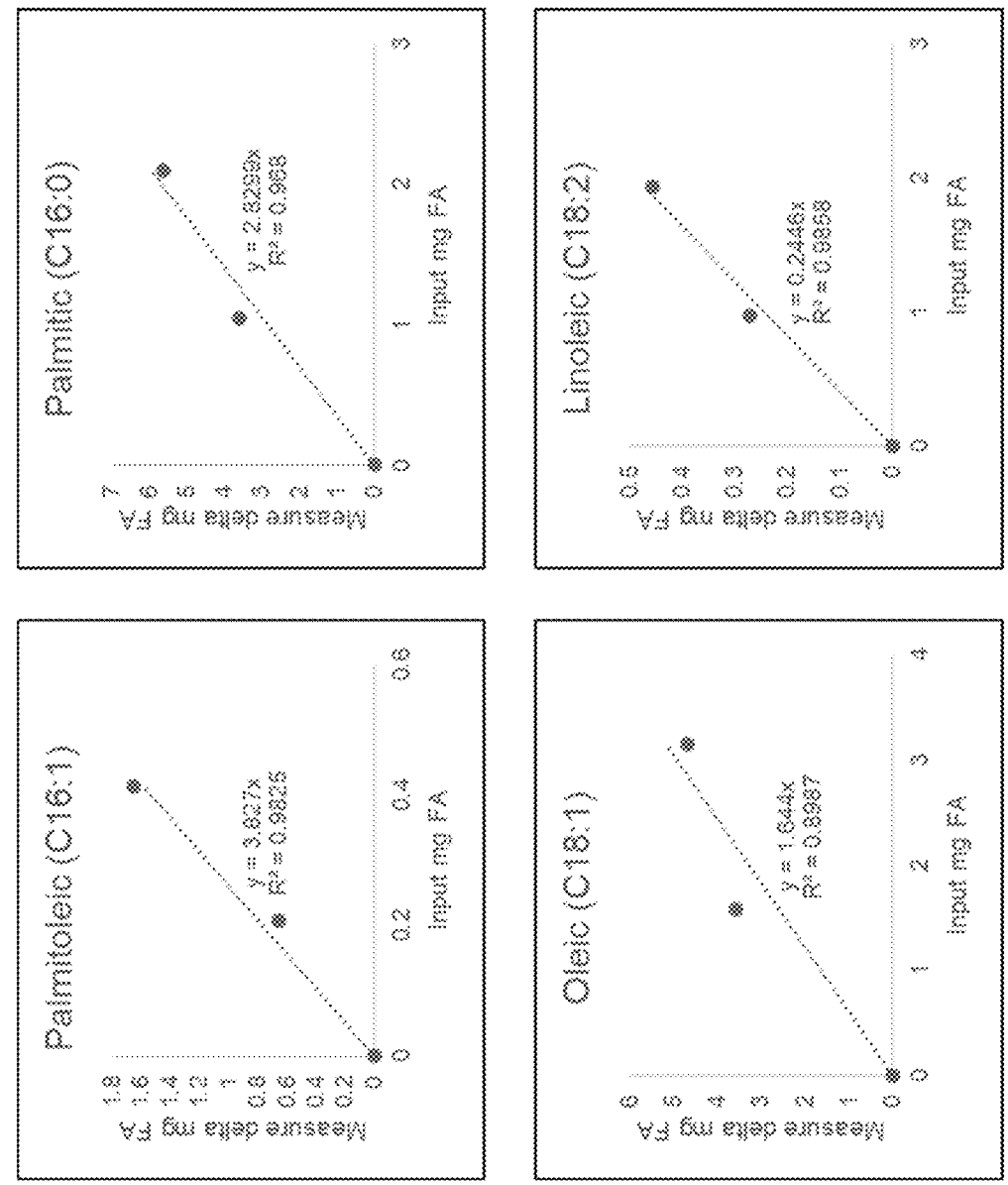
FIG. 12 shows that the titration of fatty acids into the media used for culturing cell-based meat can change the fatty acid profile of slaughter-free cell-based meat.

FIG. 12 shows the titration of FA into media to change the profile of specific FAs. Based on their prevalence in conventional chicken, four specific fatty acids, palmitoleic (C16:1), palmitic (C16:0), linoleic (C18:2), and oleic acid (C18:1), were chosen for targeted increase through supplementation into the cell culture media. Tissue were formed using a co-culture method (described Method 14 in Table 1) using culture media with enhanced levels of each fatty acid as depicted in FIG. 12 (10 mg/L total FA: 2.8 mg/L C16:0, 0.5 mg/L C16:1, 4.2 mg/L C18:1, and 2.5 mg/L C18:2; 20 mg/L total FA: 5.6 mg/L C16:0, 1.0 mg/L C16:1, 8.4 mg/L C18:1, and 5.0 mg/L C18:2).

Example 5: Analysis of Macronutrients in Cell-Based Meat Products

The meat tissues were assessed for macronutrient content including moisture, protein, and fat.

Total moisture was assayed by one of two methods, either Moisture-1 or Moisture-2. In Moisture 1, AOAC method 950.46 was employed. In short, this method employs a 2 g sample that is weighed in an aluminum dish and dried for 16-18 hours at 100-102° C. in a mechanical convection air oven. The dried sample is cooled in a desiccator and reweighed; the moisture is reported at the loss in sample weight. In Moisture-2, a >100 mg sample is added to a pre-weighed aluminum dish and dried at least overnight at 70° C. to constant mass. Other temperatures, such as 50° C. may also be used. In both Moisture-1 and Moisture-2, the mass loss of the sample post-drying is attributed to the percent of total moisture in the sample.

Total protein was assayed by one of two methods, either Protein-1 or Protein-2. In Protein-1 the AOAC method 977.14 was employed. This method is a Kjeldahl method where nitrogen in the sample is reduced to ammonia in acid under heat with a catalyst. The ammonia is then distilled with water vapor and titrated with acid. A nitrogen factor of 6.25 is used to convert the nitrogen content to crude protein. In Protein-2, a modification of the Pierce BCA assay was used. A 100 mg sample was digested in 1 M sodium hydroxide at a ratio of 0.1 g/mL under sonication for 3 hours to dissolve the sample matrix. The sample digestate was then diluted and assayed via the colorimetric Pierce BCA assay. The final µg/mL values are converted to g protein per g of wet mass using the 0.1 g/mL digestion ratio.

Total fat was assayed by one of two methods, either Fat-1 or Fat-2. In Fat-1, petroleum ether was used as a solvent to extract soluble fat from the sample matrix via AOAC method 991.36. In this method, the sample was weighed in a thimble and inserted into an extraction unit, which adds the solvent to perform the extraction via a solvent recovery system. The extraction cups were dried and weighed. In a similar fashion, Fat-2 involves a modified Folch extraction where a >250 mg sample was weighed in a pre-weighed 16 mL vial and dried overnight at 70° C.; the mass loss post-drying was attributed to moisture. The dried sample remained in the vial and underwent an extraction using a Hydranal LipoSolverCM solvent (10 mL). The vial was capped with a PTFE-lined cap and shaken at 200 rpm at room temperature for 24 hours. Post-extraction, the samples were filtered through a pre-weighed PTFE filter (0.2 µm pore size) and dried at 50° C. for 48 hours, venting to a chemical fume hood. In both Fat-1 and Fat-2, the mass loss of the sample post-extraction was attributed to the percent of total fat in the sample.

Example 6: Analysis of Hormones in the Cell Culture-Based Meat Product

Meat samples were assayed for hormone levels by a 3rd party analytical laboratory (Eurofins Central Analytical Laboratories) using a LC-MS/MS method with internal reference. Hormone ELISA assay results indicated that the conventional chicken meat sample yielded higher hormone concentration compared to the cell-based meat chicken samples (grown as adherent or suspension cultures). Additional data will be collected to confirm the validity of this assay for the sample matrices of interest. Briefly, the 17β-estradiol assay was performed using the RIDASCREEN® 17β-Östradiol kit from R-biopharm. In a glass vial with a PTFE-lined cap, 1-1.5 g of wet meat sample was measured out and homogenized in 67 mM phosphate buffered saline (PBS) at a ratio of 1 mL buffer to 1 g of wet sample mass using a handheld homogenizer with a sawtooth accessory. Post-homogenization, 5 mL of methyl tert-butyl ether (MTBE) were added and then shaken for 30 min. The sample tube was centrifuged, and the MTBE supernatant layer was collected and an additional 5 mL extraction of MTBE was performed on the sample; both MTBE layers were combined for subsequent use. The MTBE solvent was evaporated overnight at 40° C. and then 1 mL of 80% methanol was added to the "dried" vial, vortexed to mix, and then 2 mL of 20 mM PBS was added and vortexed. The resultant solution was passed through a RIDA® C18 column that was pre-rinsed with methanol and conditioned with 20 mM PBS. After the sample fraction was passed through the column, the column was cleaned with a 40% methanol solution (layer discarded), then dried under a nitrogen gas stream, and the final sample was collected by passing 80% methanol through the column and collecting the layer. The sample was dried using a vacuum concentrator and then resuspended in 50 µL of buffer just prior to analysis. The kit was used according to manufacturer specifications, using a calibration range of 0 to 12.8 µg/L. Absorbance of the plate was finally measured using a plate reader and the sample values were determined according to the derived calibration curve. The assay output was in units of µg/L which were converted to ng/kg using the initial sample preparation ratio (1 g sample to 1 mL extraction buffer).

Mass spectrometry methods did not have suitable limits of detection (LOD) for the hormone analytes of interest to yield quantitative recovery for samples the levels in the cell-based meat were very low or non-existent. For instance, the hormones testosterone, progesterone, and 17β-estradiol have LOD values of 1, 1, and 20 µg/kg, respectively. MS chromatographs did not show any bands corresponding to these hormones in the cell-based meat samples. Table 15 shows a summary of LC-MS/MS results. All hormones returned as not detected (ND) or less than the limit of detection ELISA results for 17β-estradiol indicated that cell-based chicken samples yielded a lower concentration compared to conventional chicken and beef samples. 17-estradiol levels were on average 35 ng estradiol/kg wet mass for cell-based meat using the ELISA kit whereas conventional chicken, procured from the local grocery, was 90 ng/kg estradiol/kg wet mass. Negative controls in subsequent studies were in the 30 ng/kg estradiol/kg wet mass range indicating that cell-based meat samples also had levels that were near or below the limit of detection for both assays. Table 16 shows 17β-estradiol levels, using an ELISA-based method to assay conventional and cell-based chicken meat.

TABLE 15

Hormonal Levels in Cell-Based Meat Samples

| Parameter | Concentration (µg/kg) |
| --- | --- |
| Testosterone | <1 |
| Epitestosterone | <10 |
| Clostebol | NR |
| Methyltestosterone | <10 |
| Testosterone propionate | NR |
| Boldenone | <10 |
| 17α-Boldenone | <10 |
| Dianabol | <10 |
| 17α-Trenbolone | <10 |
| Trenbolone | <10 |
| 16-Hydroxystanozolole | NR |
| Stanozolol | NR |
| Nandrolone | <10 |
| Trenbolone-acetate | <10 |
| 17α-Ethinylestradiol | NR |
| 17α-Estradiol | <20 |

TABLE 15-continued

Hormonal Levels in Cell-Based Meat Samples

| Parameter | Concentration (μg/kg) |
| --- | --- |
| 17β-Estradiol | <20 |
| Dienestrol | <10 |
| Diethylstilbestrol | <10 |
| Estriol | <10 |
| Estrone | <5.0 |
| Hexestrol | <5 |
| α-Zearalanol | <10 |
| β-Zearalanol | <10 |
| Progesterone | <1.0 |
| Medroxyprogesterone | NR |
| Melengestrole acetate | <10 |
| Chlormadinone acetate | <10 |
| 17α-Hydroxyprogesterone | <10 |
| Cortisone | <10 |
| Hydrocortisone | <10 |
| Fludrocortisone acetate | <10 |

TABLE 16

17β-estradiol Levels

| Sample | ng/kg 17β-estradiol |
| --- | --- |
| Chicken | 89 |
| Gallus (chicken) fibroblast/myoblast tissue 4 (Table 1) | 34 |
| Gallus (chicken) myoblast cells 2 (Table 1) | 36 |

Example 7: Analysis of Cooked Texture in the Cell Culture-Based Meat Product

The cell-based meat samples were assessed for physical properties of significance to the human perception of texture, including "cooked bite force" and "cooked hardness".

Analysis was conducted on meat products generated from cells grown in adherent culture which had undergone a forced air dehydration process to adjust moisture content to between 65% to 85%. Dehydration occurs at temperatures below 100° F. so as not to "cook" or otherwise denature components within the meat products.

Analysis of all samples was performed by the company using a TA.XTplus Texture Analyzer equipped with a 5 kg load cell. Samples for analysis have a mass of 400 mg+/−40 mg and were packed in a cylindrical container 10.4 mm in diameter and 17 mm in height. Cooked samples were held at 150° F. in a water bath inside their individual sealed containers for 90 minutes and chilled prior to analysis.

"Cooked Bite Force" was measured using a stainless steel TA-45 incisor probe under the test settings:
(a) Test Mode Compression
(b) Pre-Test Speed 3.00 mm/sec
(c) Test Speed 3.00 mm/sec
(d) Post-Test Speed 10.00 mm/sec
(e) Target Mode Strain
(f) Force 100.0 g
(g) Distance 5.000 mm
(h) Strain 98.0%
(i) Trigger Type Auto (Force)
(j) Trigger Force 1.0 g
(k) Trigger Distance 2.000 mm
(l) Break Mode Off
(m) Break Sensitivity 10.0 g
(n) Break Detect Stop
(o) Stop Plot At Start Position
(p) Tare Mode Auto
(q) Temperature Set Point 40.0° C.
(r) Advanced Options Off "Cooked Hardness" was measured using a stainless steel TA-24 cylindrical probe under the test settings:
(a) Pre-Test Speed 2.00 mm/sec
(b) Test Speed 1.00 mm/sec
(c) Post-Test Speed 5.00 mm/sec
(d) Target Mode Strain
(e) Force Threshold 0
(f) Distance 10.000 mm
(g) Strain 40.0%
(h) Time 5.00 sec
(i) Trigger Type Auto (Force)
(j) Trigger Force 1.0 g
(k) Trigger Distance 2.000 mm
(l) Break Mode Off
(m) Break Sensitivity 10.0 g
(n) Tare Mode Auto
(o) Temperature 4.0° C.
(p) Advanced Options On
(q) Control Oven Disabled
(r) Wait For Temperature Yes
(s) Temperature Zone±0.0° C.
(t) Frame Deflection Correction Off (XT2 compatibility)

Table 17 shows the cooked texture of the cell-based meat samples. FIG. 13 shows the cooked hardness of co-culture and fibroblast monoculture tissues.

TABLE 17

Cooked Texture

Cooked Texture of Cell-Based Meat Samples

| | Cooked Hardness (g) | Cooked Bite Force (g) |
| --- | --- | --- |
| Min | 284 | 449 |
| Max | 1903 | 2966 |
| Mean | 947 | 1343 |
| Median | 779 | 1198 |
| N | 33 | 66 |

Example 8: Vitamin E Levels in Cell-Based Meat

Cell-based meat has higher enrichment of α-tocopherol (Vitamin E). Table 18 shows the amount of Vitamin E in an exemplary cell-based meat sample, has about 0.90 mg Vitamin E/100 g wet mass of cell-based meat compared to conventional meat (Table 18). Vitamin E was determined using an outside laboratory, Certified Labs, according to UPLC method AOAC 2001.13.

TABLE 18

Vitamin E Levels

| Sample | n | Mean value | Std Dev |
| --- | --- | --- | --- |
| Cell-based meat | 3 | 0.90 mg/100 g | 0.08 mg/100 g |
| Conventionally produced chicken | 27 | 0.28 mg/100 g | 0.12 mg/100 g |

Example 9: Determination of Shelf Life

Methodology I: 0.5-1.5 g of conventional or cell-based meat was aliquoted into clean, new 15 mL falcon tubes. Samples were all frozen at −80° C. in tubes. Frozen sample tubes were then removed from the −80° C. and allowed to sit at room temperature for 0, 1, 2, 7, 14, and 28 days.

After the designated number of days had passed, sample tubes were opened and serial dilutions were made using Butterfields formulation. Serial dilutions were plated on agar plates (40 g/L of Miller LB Agar powder)—100 uL of solution and spread with ethanol/flame sterilized spreader. Dilutions were $10^{-1}$ e.g. 1 g into 9 ml. Two plates were prepared for each sample dilution—all plates were incubated at 37° C. for 48 hours and photographed at 0, 24, and 48 hours. Table 19 shows the results.

TABLE 19

Shelf Life at Room Temperature

|  | 0 days | 1 day | 2 day | 7 day | 14 day | 28 days |
|---|---|---|---|---|---|---|
| Cell-based meat | ND | ND | ND | ND | ND | ND |
| Duck | ND | TNTC | TNTC | TNTC | TNTC | TNTC |
| Chicken | ND | TNTC | TNTC | TNTC | TNTC | TNTC |

TNTC = Too numerous to count
ND = Non detect

Methodology II: 1.0 g of conventional or in-vitro cell-based meat was aliquoted into clean, new 15 mL falcon tubes. Samples were stored at 4° C. or 25° C. (room temperature) for 3 days.

After the 3 days had passed, sample tubes were opened and serial dilutions were made using Butterfields formulation. Serial dilutions were plated on agar plates for Total microbial count (TC) or *E. coli*/coliform count (EC)—1 ml of solution was added to compact Dry plates as above. Dilutions were $10^{-1}$ e.g. 1 g into 9 ml were prepared. Three plates were prepared for each sample dilution—all plates incubated at 37° C. for 48 hours and photographed at 0, 24, and 48 hours. Table 20 shows the results.

TABLE 20

Shelf Life at Room Temperature, 3 days, EC and TC Counts

| Method ID | Sample ID | Storage temperature [C.] | EC counts (cfu/mL) | TC counts (cfu/mL) |
|---|---|---|---|---|
| 10 | Conventional chicken | 4 | ND | 2 |
| 10 | Cell-based meat (harvest) | 4 | ND | ND |
| 10 | Cell-based meat (formulated) | 4 | ND | ND |
| 10 | Control (blank tube) | 4 | ND | ND |
| 10 | Conventional chicken | 25 | 5.80E+06 | 7.40E+07 |
| 10 | Cell-based meat (harvest) | 25 | ND | ND |
| 10 | Cell-based meat (formulated) | 25 | ND | 8.70E+06 |
| 10 | Control (blank tube) | 25 | ND | ND |

Additional assays were carried out to assess shelf life for longer periods of time, using the methods provided above. After the designated number of days had passed at 4° C., sample tubes were opened and serial dilutions were made using Butterfields formulation. Serial dilutions were plated on agar plates and Total aerobic bacterial count was assessed. Table 21 shows the results.

TABLE 21

Shelf Life at 4° C., 0-148 days, Total Aerobic Bacteria Count (cfu/g)

| | Day | | | | | |
|---|---|---|---|---|---|---|
| | 0 | 2 | 3 | 14 | 30 | 148 |
| Conventional chicken | 0 | 16 | 17 | 73 | 6854 | 1492063 |
| Normal cell-based chicken harvest | 0 | 0 | 0 | 0 | 442 | 0 |
| Aseptic cell-based chicken harvest | 0 | 0 | 0 | 0 | 49 | 0 |

Additional assays were carried out to assess shelf life, in particular to determine *E. coli* and coliforms count, at 4° C. and 23° C., out to 148 days. Tables 22-24 show the results. Table 22 show the *E. coli* and coliform counts as cfu/g, at 4° C., at Day 148. Tables 23 and 24 shows the *E. coli* (Table 23) and coliform (Table 24) counts at 23° C. at Day 0, 1, 2, 3, 7, 30, and 148. TMTC designates too many colonies to count.

TABLE 22

Shelf Life at 4° C., 148 Days, *E. Coli* and Coliforms Count

| | DAY 148 | |
|---|---|---|
| 4° C. Sample | *E. coli* (cfu/g) | Coliforms (cfu/g) |
| Conventional chicken | 0 | 990476 |
| Cell-based meat harvest | 0 | 0 |
| Aseptic cell-based meat harvest | 0 | 0 |
| Cell-based meat formulated | 0 | 0 |
| Aseptic cell-based meat formulated | 0 | 0 |

TABLE 23

Shelf Life, 23° C., 0-148 Days, *E. Coli* Count

| 23° C., *E. Coli* | DAY 0 | DAY 1 | DAY 2 | DAY 3 | DAY 7 | DAY 30 | DAY 148 |
|---|---|---|---|---|---|---|---|
| Conventional chicken | 3.23E+00 | 1.33E+06 | 4.07E+06 | 3.84E+07 | 9.75E+06 | Terminated | |
| Cell-based meat harvest | 0.00E+00 | 0.00E+00 | 0.00E+00 | 0.00E+00 | 0.00E+00 | 0.00E+00 | 0.00E+00 |
| Aseptic Cell-based meat harvest | 0.00E+00 | 0.00E+00 | 0.00E+00 | 0.00E+00 | 0.00E+00 | 0.00E+00 | 0.00E+00 |
| Cell-based meat formulated | 0.00E+00 | 0.00E+00 | 0.00E+00 | 0.00E+00 | 0.00E+00 | 0.00E+00 | 0.00E+00 |
| Aseptic Cell-based meat formulated | 0.00E+00 | 0.00E+00 | 0.00E+00 | 0.00E+00 | 0.00E+00 | 0.00E+00 | 0.00E+00 |

TABLE 24

Shelf Life, 23° C., 0-148 Days, Coliforms Count

| 23° C., Coliforms (cfu/g) | DAY 0 | DAY 1 | DAY 2 | DAY 3 | DAY 14 | DAY 30 | DAY 148 |
|---|---|---|---|---|---|---|---|
| Conventional chicken | 0.00E+00 | 0.00E+00 | 6.11E+06 | 5.77E+06 | 7.47E+05 | Terminated | |
| Cell-based meat harvest | 0.00E+00 | 0.00E+00 | 0.00E+00 | 0.00E+00 | 0.00E+00 | 0.00E+00 | 0.00E+00 |
| Aseptic Cell-based meat harvest | 0.00E+00 | 0.00E+00 | 0.00E+00 | 0.00E+00 | 0.00E+00 | 0.00E+00 | 0.00E+00 |
| Cell-based meat formulated | 0.00E+00 | 0.00E+00 | 0.00E+00 | 0.00E+00 | 0.00E+00 | 0.00E+00 | 0.00E+00 |
| Aseptic Cell-based meat formulated | 0.00E+00 | 0.00E+00 | 0.00E+00 | 0.00E+00 | 0.00E+00 | 0.00E+00 | 0.00E+00 |

The invention claimed is:

1. A slaughter-free poultry product for dietary consumption exhibiting an extended shelf life, wherein the shelf life is extended for greater than 14 days following harvest compared to conventional meat obtained by slaughter,
wherein the slaughter-free poultry product comprises the following fatty acid classes in the amounts indicated, expressed as % of that class over total fatty acids:
saturated fatty acids content between 10% to 30%;
monounsaturated fatty acids content between 45% to 60%; and
polyunsaturated fatty acids content between 1% to 10%;
wherein the slaughter-free poultry product is produced with a media that is substantially free of serum;
and wherein the extended shelf life of the slaughter-free poultry is due at least in part to the lower total fatty acid content which reduces fatty acid oxidation and to being produced with the media that is substantially free of serum.

2. The slaughter-free poultry product of claim 1, wherein the slaughter-free poultry product exhibits an extended shelf life at 4° C.

3. The slaughter-free poultry product of claim 1, wherein the slaughter-free poultry product exhibits an extended shelf life at 23° C.

4. The slaughter-free poultry product of claim 1, wherein the shelf life is determined by measuring the total microbial count (TC), *E. coli*/coliforms count (EC), *E. coli* microbial count, or the coliforms count.

5. The slaughter-free poultry product of claim 1, wherein the shelf life threshold is no more than 1 cfu microbial contamination per g/wet mass.

6. The slaughter-free poultry product of claim 1, wherein the shelf life is determined after harvest, and prior to formulation.

7. The slaughter-free poultry product of claim 1, wherein the shelf life is determined after formulation.

8. The slaughter-free poultry product of claim 6, wherein the shelf life is extended when the meat is harvested under non-aseptic conditions.

9. The slaughter-free poultry product of claim 4, wherein the TC measurement of conventional meat obtained by slaughter is at least 1.5× higher than that of the TC measurement of slaughter-free poultry product.

10. The slaughter-free poultry product of claim 1, wherein the slaughter-free poultry product comprises no more than about 1 μg steroid hormone.

11. The slaughter-free poultry product of claim 1, wherein the slaughter-free poultry product comprises about 50 g to about 90 g by weight of amino acids per 100 g dry mass.

12. The slaughter-free poultry product of claim 1, wherein the slaughter-free poultry product comprises one or more of the following amino acids in the indicated amounts (expressed as g of amino acid/100 g total amino acid): Tryptophan about 1 to about 2.2, Threonine about 4.6 and 6.5, Isoleucine about 3.8 to about 5, Leucine about 6.1 to about 8.9, Lysine about 5.7 to about 8.8, Methionine about 0.14 to about 3.0, Cysteine about 1.5 to about 1.8, Phenylalanine about 3.7 to about 4.8, Tyrosine about 3.0 to about 5.2, Valine about 4.8 to about 6.1, Arginine about 7.0 to about 8.0, Histidine about 2.5 to about 4, Alanine about 5.0 to about 6.3, Aspartic acid about 8.6 to about 10.4, Glutamic acid about 12.5 to about 14.6, Glycine about 4.6 to about 9.8, Proline about 4.6 to about 6.8, Serine about 4.4 to about 5.3, and/or Hydroxyproline about 0.0 to 4.0.

13. The slaughter-free poultry product of claim 1, wherein the slaughter-free poultry product has a moisture content of about 65% to about 95%, wherein the moisture content is measured after harvest, but before formulation.

14. The slaughter-free poultry product of claim 1, wherein the slaughter-free poultry product comprises at least about 0.5 mg Vitamin E/100 g wet mass of the slaughter-free poultry product.

15. The slaughter-free poultry product of claim 1, wherein the slaughter-free poultry product comprises a ratio of about 2:1 to 18:1 omega 6:3 fatty acids classes.

16. The slaughter-free poultry product of claim 1, wherein the slaughter-free poultry product is substantially free of vasculature.

17. The slaughter-free poultry product of claim 1, wherein the conventional meat is not processed.

* * * * *